(12) United States Patent
Medoff et al.

(10) Patent No.: US 8,714,810 B2
(45) Date of Patent: *May 6, 2014

(54) PROCESSING BIOMASS

(71) Applicant: Xyleco, Inc., Woburn, MA (US)

(72) Inventors: Marshall Medoff, Brookline, MA (US); Thomas Craig Masterman, Brookline, MA (US)

(73) Assignee: Xyleco, Inc., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,306

(22) Filed: May 24, 2013

(65) Prior Publication Data

US 2013/0252283 A1     Sep. 26, 2013

Related U.S. Application Data

(63) Continuation of application No. 12/782,694, filed on May 18, 2010.

(60) Provisional application No. 61/179,995, filed on May 20, 2009, provisional application No. 61/218,832, filed on Jun. 19, 2009.

(51) Int. Cl.
*B01F 15/00* (2006.01)
*C12N 9/14* (2006.01)
*C12P 19/02* (2006.01)

(52) U.S. Cl.
USPC .................. 366/163.2; 435/195; 435/105

(58) Field of Classification Search
None
See application file for complete search history.

(56) References Cited

U.S. PATENT DOCUMENTS

| | | | |
|---|---|---|---|
| 3,334,868 A | 8/1967 | Lage | |
| 4,176,522 A | 12/1979 | Holtzapple et al. | |
| 4,243,750 A | 1/1981 | Muller et al. | |
| 4,426,450 A | 1/1984 | Donofrio | |
| 5,779,996 A | 7/1998 | Stormo | |
| 6,455,306 B1 | 9/2002 | Goldstein et al. | |
| 2003/0211130 A1 | 11/2003 | Sanders et al. | |
| 2004/0050764 A1 | 3/2004 | Perriello | |
| 2004/0053373 A1 | 3/2004 | Foody et al. | |
| 2007/0172945 A1 | 7/2007 | O'Kennedy et al. | |
| 2007/0200262 A1 | 8/2007 | Hills | |
| 2008/0139865 A1 | 6/2008 | Galliher et al. | |
| 2008/0193991 A1 | 8/2008 | Allen et al. | |
| 2008/0202504 A1 | 8/2008 | Hilst | |

FOREIGN PATENT DOCUMENTS

| | | |
|---|---|---|
| BE | 414030 | 3/1936 |
| CN | 2142464 | 9/1993 |
| CN | 2334762 | 8/1999 |
| CN | 2762897 | 3/2006 |
| CN | 1844347 | 10/2006 |
| DE | 2310256 | 9/1973 |
| GB | 470898 | 8/1937 |
| JP | 1017701 | 1/1989 |
| JP | 2006121954 | 5/2006 |
| JP | 2009045037 | 3/2009 |

OTHER PUBLICATIONS

Myers et al. "Optimize Mixing by Using the Proper Baffles" CEP Feb. 2002, pp. 42-47.*
Olofsson et al. "A short review on SSF—an interesting process option for ethanol production from lignocellulosic feedstocks" Biotechnology for Biofuels 2008, 1:7, 14pgs.*
Wales "Mixing and Agitation" Chapter 10, Chemical Process Equipment Selection and Design 1990, pp. 287-304.
Onishi et al. "Feasibility Study on Using a Single Mixer Pump for Tank 241-AN-101 Waste Retrieval" PNNL-14105, 54 pages, Jan. 2003.
ISR and Written Opinion for PCT/US2010/035315, EPO as ISA, mailed Feb. 4, 2011, 18 pages.

* cited by examiner

*Primary Examiner* — Thane Underdahl
(74) *Attorney, Agent, or Firm* — Leber Patent Law PC

(57) ABSTRACT

Biomass feedstocks (e.g., plant biomass, animal biomass, and municipal waste biomass) are processed to produce useful products, such as fuels. For example, systems are described that can convert feedstock materials to a sugar solution, which can then be fermented to produce ethanol. Biomass feedstock is saccharified in a vessel by operation of a jet mixer, the vessel also containing a fluid medium and a saccharifying agent.

10 Claims, 27 Drawing Sheets

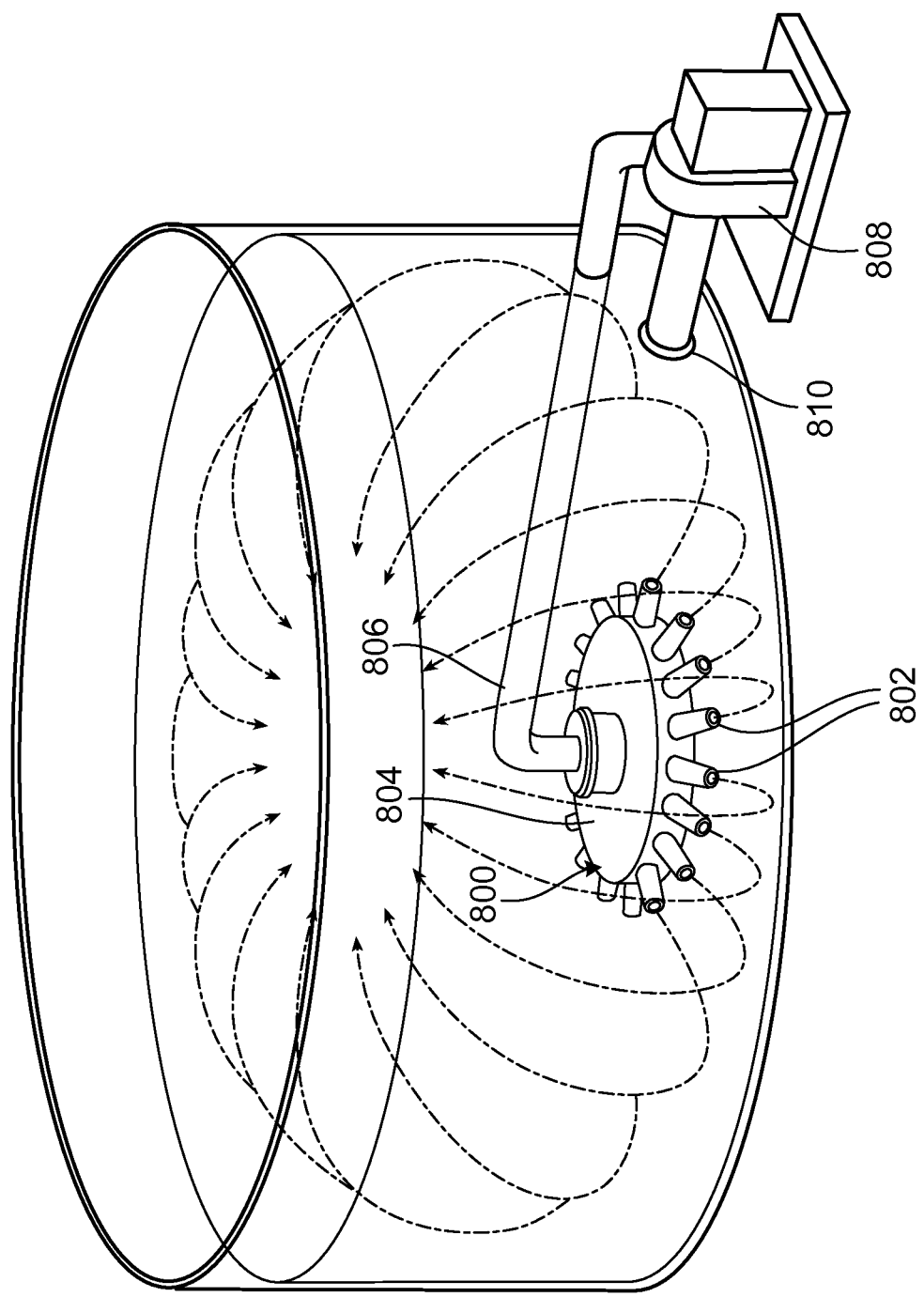

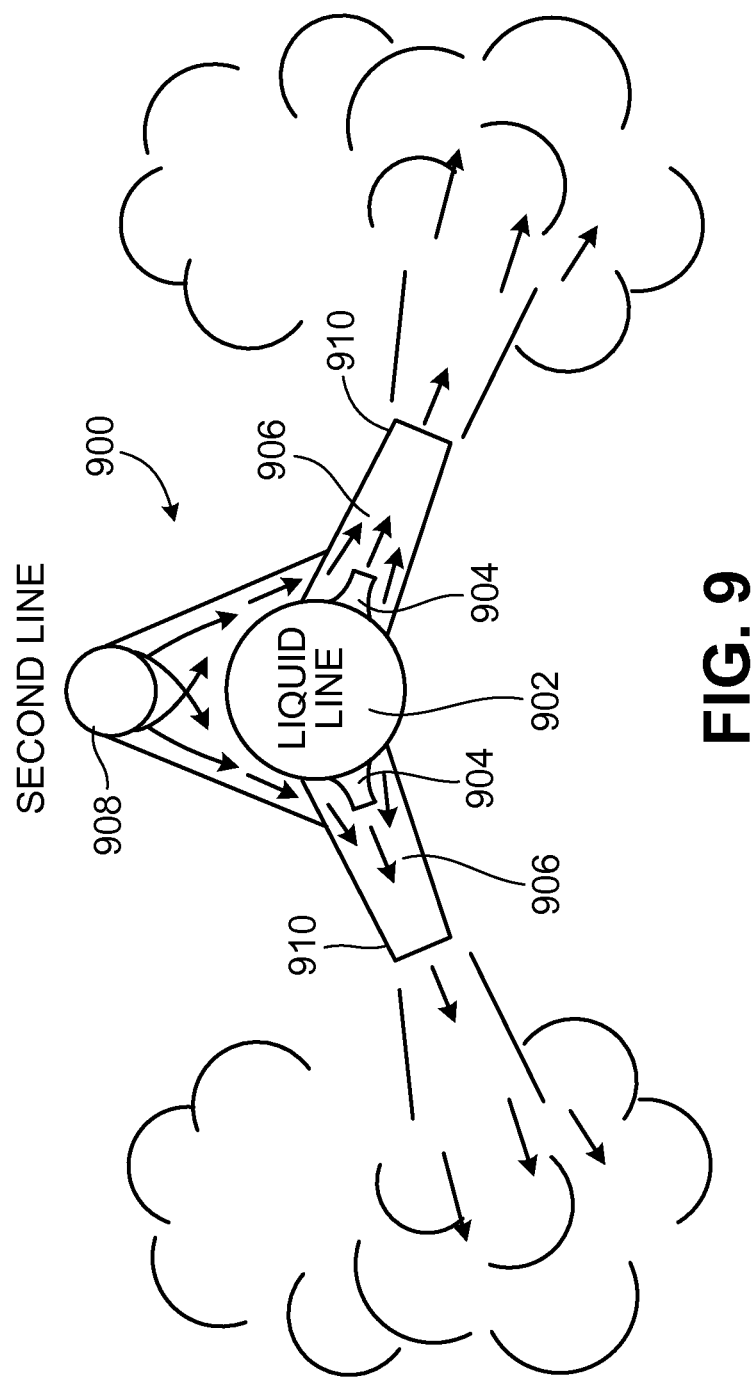

PROCESSING BIOMASS

RELATED APPLICATIONS

This application is a continuation of U.S. Ser. No. 12/782,694, filed May 18, 2010, which claims priority to U.S. Provisional Application Ser. No. 61/179,995, filed May 20, 2009, and U.S. Provisional Application Ser. No. 61/218,832, filed Jun. 19, 2009. The complete disclosure of each of these provisional applications is hereby incorporated by reference herein.

BACKGROUND

Cellulosic and lignocellulosic materials are produced, processed, and used in large quantities in a number of applications. Often such materials are used once, and then discarded as waste, or are simply considered to be waste materials, e.g., sewage, bagasse, sawdust, and stover.

Various cellulosic and lignocellulosic materials, their uses, and applications have been described in U.S. Pat. Nos. 7,307,108, 7,074,918, 6,448,307, 6,258,876, 6,207,729, 5,973,035 and 5,952,105; and in various patent applications, including "FIBROUS MATERIALS AND COMPOSITES," PCT/US2006/010648, filed on Mar. 23, 2006, AND "FIBROUS MATERIALS AND COMPOSITES," U.S. Patent Application Publication No. 2007/0045456.

SUMMARY

Generally, this invention relates to processes for saccharifying or liquifying a material, e.g., a cellulosic or lignocellulosic feedstock, by converting the cellulosic portion of the material to low molecular weight sugars, e.g., using an enzyme. The invention also relates to converting a feedstock to a product, e.g., by fermentation.

The processes disclosed herein can utilize low bulk density materials, for example cellulosic or lignocellulosic feedstocks that have been physically pretreated to have a bulk density of less than about 0.5 g/cm$^3$, e.g., less than about 0.35 g/cm$^3$, 0.25 g/cm$^3$, 0.20 g/cm$^3$, 0.15 g/cm$^3$, 0.10 g/cm$^3$, 0.05 g/cm$^3$ or less, e.g., 0.025 g/cm$^3$.

Such materials can be especially difficult to mix with liquids, e.g., with water or a solvent system for saccharification, fermentation, or other processing. Due to their low bulk density, the materials tend to float to the surface of the liquid rather than being dispersed therein. In some cases, the materials can be hydrophobic, highly crystalline, or otherwise difficult to wet. At the same time, it is desirable to process the feedstock in a relatively high solids level dispersion, in order to obtain a high final concentration of sugar in the saccharified material, or a high concentration of the desired product after processing (e.g., of ethanol or other alcohol(s) after fermentation). In some cases, utilizing the methods described herein the solids level of the dispersion during processing can be, for example, at least 20, 25, 30, 35, 40, 45, or even at least 50 percent by weight dissolved solids.

The inventors have found that dispersion of a feedstock in a liquid mixture can be enhanced, and as a result the solids level of the mixture can be increased, by the use of certain mixing techniques and equipment. The mixing techniques and equipment disclosed herein also enhance mass transfer, and as a result reaction rates in a mixture, and avoid or minimize harm to sensitive ingredients of the mixture such as microorganisms and enzymes. In particular, jet mixing techniques, including for example jet aeration and jet flow agitation, have been found to provide good wetting, dispersion and mechanical disruption. By increasing the solids level of the mixture, the process can proceed more rapidly, more efficiently and more cost-effectively, and the resulting concentration of the final product can be increased.

Some of the processes disclosed herein include saccharification of a feedstock, and transportation of the feedstock from a remote location, e.g., where the feedstock is produced or stored, to the manufacturing facility. In some cases, saccharification can take place partially or entirely during transport. In such cases, it can be advantageous to provide mixing, e.g., jet mixing, in the transport vessel. In some cases, saccharification can be completed during transport. In some instances, fermentation can take place partially or entirely during transport.

In some implementations, the process further includes reducing the recalcitrance of a feedstock, before or during saccharification. The process may include the further steps of measuring the lignin content of the feedstock and determining whether pretreatment is needed and under what conditions based on the measured lignin content.

In one aspect, the invention features a method that includes saccharifying a biomass feedstock by mixing the feedstock with a liquid medium and a saccharifying agent in a vessel, using a jet mixer.

Some embodiments include one or more of the following features. The feedstock can have a bulk density of less than about 0.5 g/cm$^3$. The feedstock may be, for example, a cellulosic or lignocellulosic material. The liquid can include water. The saccharifying agent can include an enzyme. The jet mixer may include, for example, a jet-flow agitator, a jet aeration type mixer, or a suction chamber jet mixer. If a jet aeration type mixer is used, it may be used without injection of air through the jet mixer. For example, if the jet aeration type mixer includes a nozzle having a first inlet line and a second inlet line, in some cases both inlet lines are supplied with a liquid. In some cases, mixing comprises adding the feedstock to the liquid medium in increments and mixing between additions. The method may further include monitoring the glucose level of the mixture of feedstock, liquid medium and saccharifying agent during mixing, and in some cases adding additional feedstock and saccharifying agent to the vessel during saccharification. The mixing vessel may be, for example, a tank, rail car or tanker truck. Saccharification can in some cases take place partially or completely during transport of the mixture of feedstock, liquid medium and saccharifying agent. The method may further include adding an emulsifier or surfactant to the mixture in the vessel.

In another aspect, the invention features saccharifying a biomass feedstock by mixing the feedstock with a liquid medium and a saccharifying agent in a vessel, using a mixer that produces generally toroidal flow within the vessel.

In some embodiments, the mixer is configured to limit any increase in the overall temperature of the liquid medium to less than 5° C. over the course of mixing. This aspect may also include, in some embodiments, any of the features discussed above.

In yet a further aspect, the invention features a method that includes converting a low molecular weight sugar to a product by mixing the low molecular weight sugar with a microorganism in a liquid medium, using a jet mixer.

Some embodiments include one or more of the following features. The liquid medium can include water. The microorganism can include yeast. The jet mixer can include a jet-flow agitator, jet aeration type mixer, or suction chamber jet mixer.

In another aspect, the invention features an apparatus that includes a tank, a jet mixer having a nozzle disposed within the tank, a delivery device configured to deliver a biomass feedstock to the tank, and a delivery device configured to deliver a metered amount of a saccharifying agent to the tank.

Some embodiments include one or more of the following features. The jet mixer can further include a motor, and the apparatus can further include a device configured to monitor the torque on the motor during mixing. The apparatus can also include a controller that adjusts the operation of the feedstock delivery device and/or the saccharifying agent delivery device based on input from the torque-monitoring device.

The invention also features a method that includes saccharifying a biomass feedstock in a vessel to form a saccharified mixture; inoculating the saccharified mixture in the vessel with a microorganism; and allowing the inoculated saccharified mixture to ferment in the vessel.

In some cases, the contents of the vessel are transferred to a transport vessel during fermentation and fermentation continues in the transport vessel. The method may further include agitating the contents of the vessel with a jet mixer during saccharification and fermentation. In some embodiments, the method further includes monitoring the oxygen content and ethanol and/or sugar content of the fermenting mixture.

In another aspect, the invention features a fermentation system that includes a vessel having a vent; a source of oxygen in communication with the vessel; an oxygen monitor configured to monitor the oxygen content of a liquid in the vessel; and a controller configured to adjust the oxygen content of the liquid, using the vent and oxygen source, in response to input from the oxygen monitor.

The flow rate of oxygen into the vessel, if oxygenation is required, can be relatively low. For example, the controller may be configured to oxygenate the vessel at a rate of less than 0.2 vvm, e.g., less than 0.1, 0.05, 0.025, or even less than 0.01 vvm.

The fermentation system may further include a fermentation monitor configured to monitor the sugar concentration and/or ethanol concentration of the liquid in the vessel; and a controller configured to stop fermentation based on input received from the fermentation monitor. In some cases, the system includes a fermentation stopping module configured to stop fermentation in response to a signal received from the controller.

All publications, patent applications, patents, and other references mentioned herein or attached hereto are incorporated by reference in their entirety for all that they contain.

DESCRIPTION OF THE DRAWINGS

FIG. 8 is a diagrammatic perspective view of a tank and a jet aeration type mixing system positioned in the tank, with the tank being shown as transparent to allow the jet mixer and associated piping to be seen.

FIG. 9 is a cross-sectional view of a jet aeration type mixer according to one embodiment.

DETAILED DESCRIPTION

Figure 1:
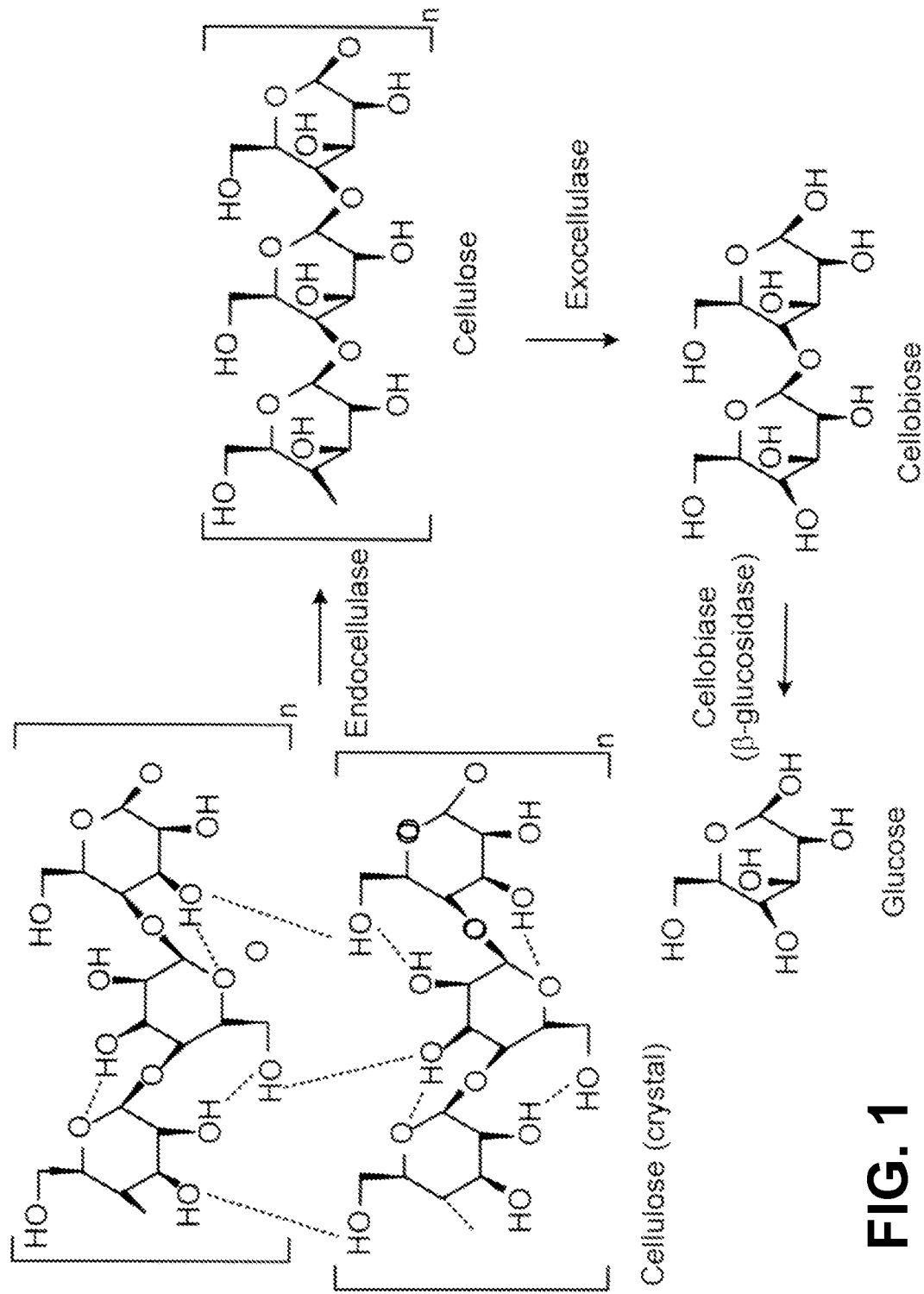
FIG. 1 is a diagram illustrating the enzymatic hydrolysis of cellulose to glucose.

Using the methods described herein, biomass (e.g., plant biomass, animal biomass, and municipal waste biomass) can be processed to produce useful intermediates and products such as those described herein. Systems and processes are described herein that can use as feedstock materials cellulosic and/or lignocellulosic materials that are readily available, but can be difficult to process by processes such as fermentation. Many of the processes described herein can effectively lower the recalcitrance level of the feedstock, making it easier to process, such as by bioprocessing (e.g., with any microorganism described herein, such as a homoacetogen or a heteroacetogen, and/or any enzyme described herein), thermal processing (e.g., gasification or pyrolysis) or chemical methods (e.g., acid hydrolysis or oxidation). Biomass feedstock can be treated or processed using one or more of any of the methods described herein, such as mechanical treatment, chemical treatment, radiation, sonication, oxidation, pyrolysis or steam explosion. The various treatment systems and methods can be used in combinations of two, three, or even four or more of these technologies or others described herein and elsewhere.

The processes disclosed herein can utilize low bulk density materials, for example cellulosic or lignocellulosic feedstocks that have been physically pretreated to have a bulk density of less than about 0.5 g/cm$^3$, e.g., less than about 0.35 g/cm$^3$, 0.25 g/cm$^3$, 0.20 g/cm$^3$, 0.15 g/cm$^3$, 0.10 g/cm$^3$, 0.05 g/cm$^3$ or less, e.g., 0.025 g/cm$^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

In order to convert the feedstock to a form that can be readily processed, the glucan- or xylan-containing cellulose in the feedstock is hydrolyzed to low molecular carbohydrates, such as sugars, by a saccharifying agent, e.g., an enzyme or acid, a process referred to as saccharification. The low molecular weight carbohydrates can then be used, for example, in an existing manufacturing plant, such as a single cell protein plant, an enzyme manufacturing plant, or a fuel plant, e.g., an ethanol manufacturing facility.

The materials that include cellulose can be treated with the saccharifying agent by combining the material and the saccharifying agent in a liquid medium, e.g., a solvent such as an aqueous solution. The saccharifying agent, material and liquid medium are mixed thoroughly, using one or more mixers having the mixing characteristics described herein, e.g., one or more jet mixers. In some implementations, the material and/or the saccharifying agent are added incrementally rather than all at once. For example, a portion of the material can be added to the liquid medium and mixed with the saccharifying agent until the material is at least partially saccharified, at which point a second portion of the material is added to the mixture. This process can continue until a desired sugar concentration is obtained.

Enzymes and biomass-destroying organisms that break down biomass, such as the cellulose and/or the lignin portions of the biomass, contain or manufacture various cellulolytic enzymes (cellulases), ligninases or various small molecule biomass-destroying metabolites. These enzymes may be a complex of enzymes that act synergistically to degrade crystalline cellulose or the lignin portions of biomass. Examples of cellulolytic enzymes include: endoglucanases, cellobiohydrolases, and cellobiases (β-glucosidases). Referring to FIG. 1, a cellulosic substrate is initially hydrolyzed by endoglucanases at random locations producing oligomeric intermediates. These intermediates are then substrates for exo-splitting glucanases such as cellobiohydrolase to produce cellobiose from the ends of the cellulose polymer. Cellobiose is a water-soluble 1,4-linked dimer of glucose. Finally cellobiase cleaves cellobiose to yield glucose. Suitable cellulases will be discussed herein in a later section.

The saccharification process can be partially or completely performed (a) in a tank (e.g., a tank having a volume of at least 4000, 40,000, 400,000, 4,000,000 or 40,000,000 L) in a manufacturing plant, and/or (b) in transit, e.g., in a rail car, tanker truck, or in a supertanker or the hold of a ship. The time required for complete saccharification will depend on the process conditions and the feedstock and enzyme used. If saccharification is performed in a manufacturing plant under controlled conditions, the cellulose may be substantially entirely converted to glucose in about 12-96 hours. If saccharification is performed partially or completely in transit, saccharification may take longer.

In some cases, saccharification is performed at a pH of about 4 to 7, e.g., about 4.5 to 6, or about 5 to 6.

It is generally preferred that the final concentration of glucose in the sugar solution be relatively high, e.g., greater than 15%, or greater than 20, 30, 40, 50, 60, 70, 80, 90 or even greater than 95% by weight. This reduces the volume to be shipped, and also inhibits microbial growth in the solution. After saccharification, the volume of water can be reduced, e.g., by evaporation or distillation.

A relatively high concentration solution can be obtained by limiting the amount of water added to the feedstock with the enzyme. The concentration can also be controlled by controlling how much saccharification takes place. For example, concentration can be increased by adding more feedstock to the solution. Solubility of the feedstock in the medium can be increased, for example, by increasing the temperature of the solution, and/or by adding a surfactant as will be discussed below. For example, the solution can be maintained at a temperature of 40-50° C., 50-60° C., 60-80° C., or even higher.

Figure 2:
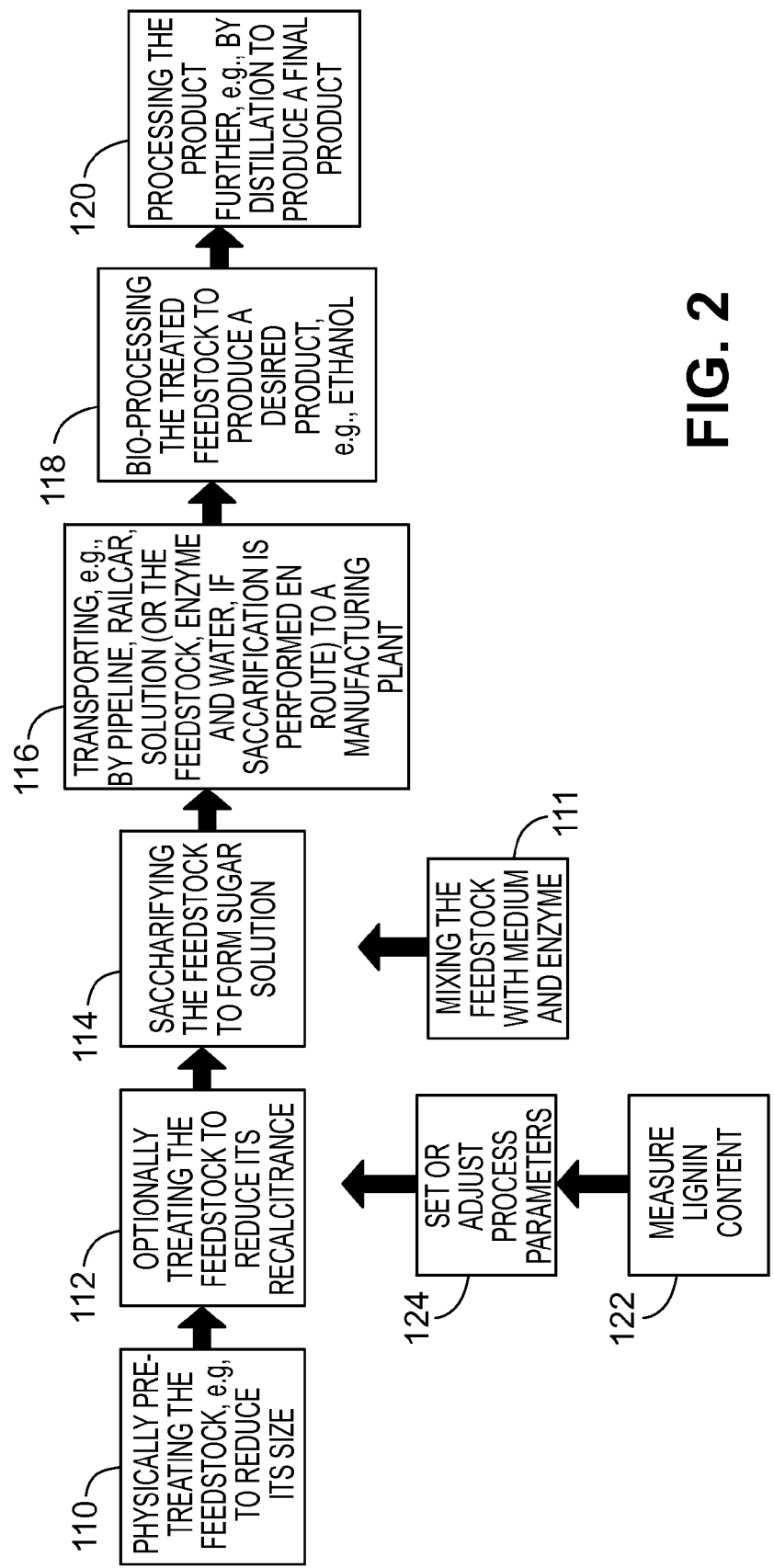
FIG. 2 is a flow diagram illustrating conversion of a feedstock to ethanol via production and transport of a glucose solution.

Referring to FIG. 2, a process for manufacturing an alcohol, e.g., ethanol, can include, for example, optionally physically pre-treating the feedstock, e.g., to reduce its size (step 110), before and/or after this treatment, optionally treating the feedstock to reduce its recalcitrance (step 112), and saccharifying the feedstock to form a sugar solution (step 114). Saccharification can be performed by mixing a dispersion of the feedstock in a liquid medium, e.g., water, with an enzyme (step 111), as will be discussed in detail below. During or after saccharification, the mixture (if saccharification is to be partially or completely performed en route) or solution can be transported, e.g., by pipeline, railcar, truck or barge, to a manufacturing plant (step 116). At the plant, the solution can be bio-processed to produce a desired product, e.g., ethanol (step 118), which is then processed further, e.g., by distillation (step 120). The individual steps of this process will be described in detail below. If desired, the steps of measuring lignin content (step 122) and setting or adjusting process parameters (step 124) can be performed at various stages of the process, for example just prior to the process step(s) used to change the structure of the feedstock, as shown. If these steps are included, the process parameters are adjusted to compensate for variability in the lignin content of the feedstock, as described in U.S. Provisional Application No. 61/151,724, filed on Feb. 11, 2009, the complete disclosure of which is incorporated herein by reference.

Figure 2A:
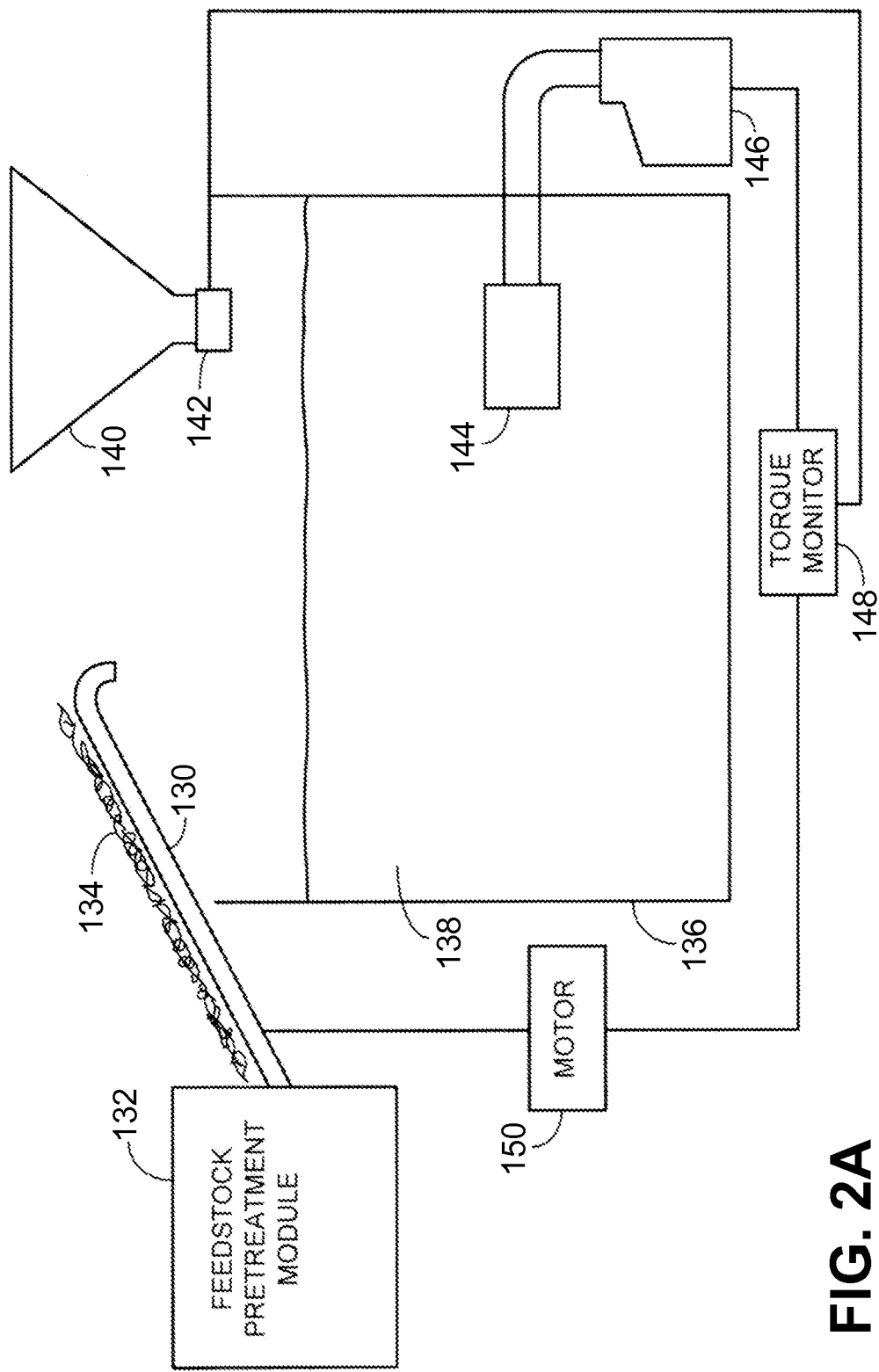
FIG. 2A is a diagrammatic illustration of a saccharification system according to one embodiment.

The mixing step 111 and saccharifying step 114 can be performed using, for example, the system shown in FIG. 2A. This system includes a conveyor 130, which receives feedstock that has been treated to reduce its size and optionally to reduce its recalcitrance (steps 110 and 112 above) by a feedstock pretreatment module 132. The feedstock 134 is delivered to a tank 136, which contains a liquid medium 138, e.g., water, which is delivered to the tank through a valved piping system (not shown). A dispersing system may be used to facilitate initial dispersion of the feedstock into the liquid medium, e.g., as disclosed in U.S. Provisional Application No. 61/296,658, filed Jan. 20, 2010, the full disclosure of which is incorporated by reference herein.

A saccharifying agent is delivered to the tank from a hopper 140, which includes a metering device 142. The contents of the tank are mixed by one or more jet mixers. A jet mixer 144 is represented diagrammatically in FIG. 2A; examples of suitable jet mixers will be described in detail below. The jet mixer produces a jet using a motor 146 that drives a pump and/or a rotor (not shown). The torque exerted by the motor 146 correlates with the solids level of the mixture in the tank, which in turn reflects the degree to which the mixture has saccharified. The torque is measured by a torque monitor 148, which sends a signal to a motor 150 that drives the conveyor 130 and also to the metering device 142 of the hopper 140. Thus, the supply of the treated feedstock and the enzyme can be interrupted and resumed as a function of the saccharification of the contents of the tank. The data measured by the torque monitor can also be used to adjust the jet mixer, e.g., to a lower RPM for a mixer that utilizes a rotor, or to a lower jet velocity for a pump-driven mixer. Instead of, or in addition to, the torque monitor, the system may include an Amp monitor (not shown) that measures the full load amperage of the motor. In some cases, the jet mixer may include a variable frequency drive (VFD) to allow the speed of the motor to be adjusted.

The system may also include a heat monitor (not shown) that monitors the temperature of the liquid medium and adjusts the feed rate of the feedstock and/or the mixing conditions in response to increases in temperature. Such a temperature feedback loop can be used to prevent the liquid medium from reaching a temperature that will denature the enzyme.

When one or more pumps are used in the systems described herein, it is generally preferred that positive displacement (PD) pumps be used, e.g., progressive cavity or screw-type PD pumps.

Figure 3:
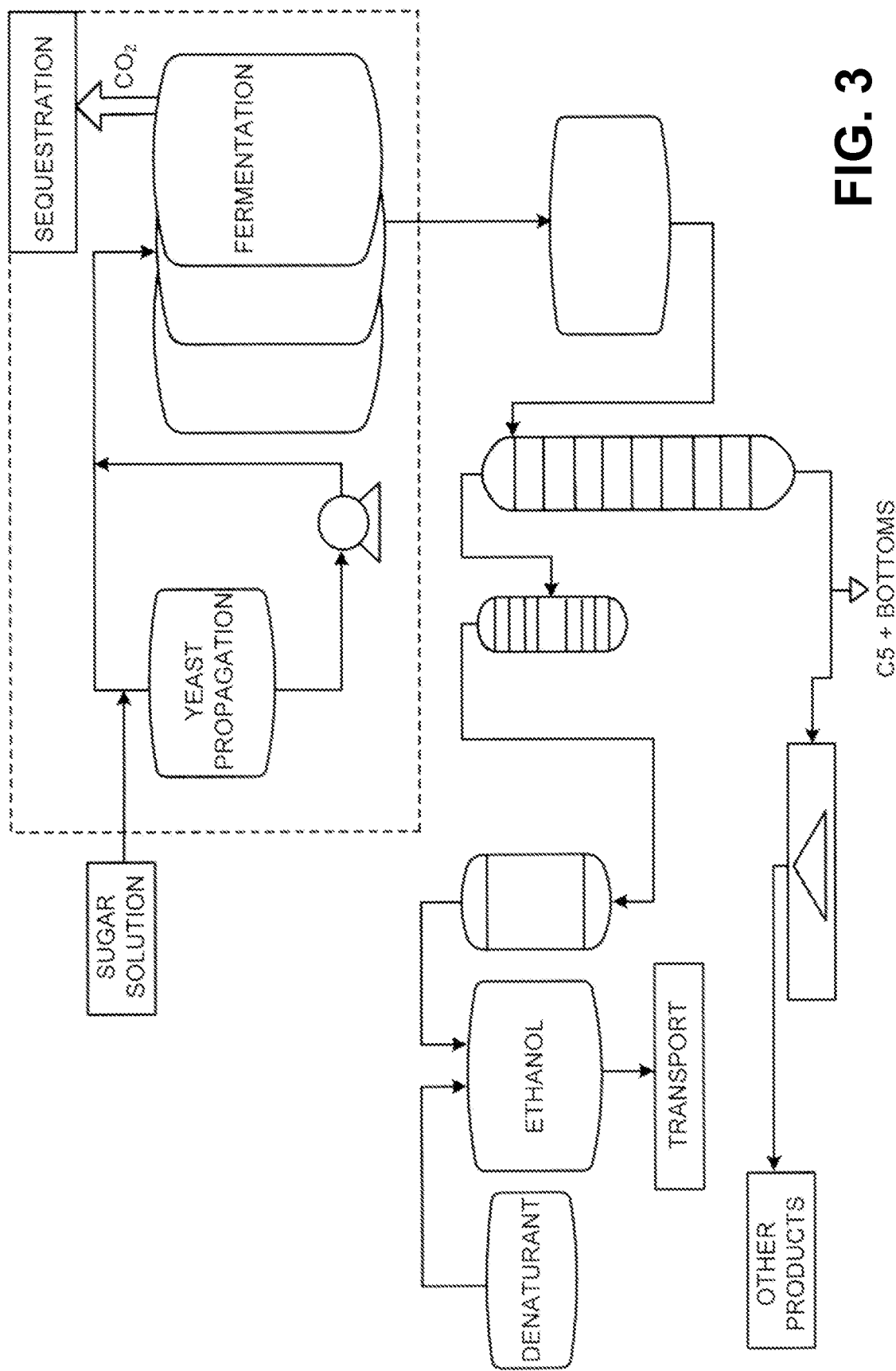
FIG. 3 is a schematic diagram of an ethanol manufacturing facility that has been retrofitted to utilize the solutions and suspensions disclosed herein.

In some cases, the manufacturing plant can be, for example, an existing grain-based or sugar-based ethanol plant or one that has been retrofitted by removing or decommissioning the equipment upstream from the bio-processing system (which in a typical ethanol plant generally includes grain receiving equipment, a hammermill, a slurry mixer, cooking equipment and liquefaction equipment). Thus, the feedstock received by the plant is input directly into the fermentation equipment. A retrofitted plant is shown schematically in FIG. 3. The use of an existing grain-based or sugar-based ethanol plant in this manner is described in U.S. Ser. No. 12/704,521, filed Feb. 11, 2010, the full disclosure of which is incorporated herein by reference.

In some embodiments, rather than transporting the saccharified feedstock (sugar solution) to a separate manufacturing plant, or even a separate tank, the sugar solution is inoculated and fermented in the same tank or other vessel used for saccharification. Fermentation can be completed in the same vessel, or can be started in this manner and then completed during transport as discussed above. Saccharifying and fermenting in a single tank are described in U.S. Provisional Application No. 61/296,673, filed Jan. 20, 2010, the full disclosure of which is incorporated herein by reference.

Generally, the oxygen level in the fermentation vessel should be controlled, e.g., by monitoring the oxygen level and venting the tank or aerating the mixture as necessary. It is also desirable to monitor the level of ethanol in the vessel, so that when the ethanol level begins to drop the fermentation process can be stopped, e.g., by heating or the addition of sodium bisulfite. Other methods of stopping fermentation include adding a peroxide (e.g., peroxy acetic acid or hydrogen peroxide), adding succinic acid or a salt thereof, cooling the contents of the vessel, or reducing the oxygen sparge rate. Combinations of any two or more of these methods may be used. If fermentation is to be conducted or completed during transport, the transportation vessel (e.g., the tank of a rail car or tanker truck) can be fitted with a control unit that includes an oxygen monitor and ethanol monitor, and a delivery system for delivering sodium bisulfite (or other fermentation terminating additive) to the tank and/or a system for adjusting the parameters in the tank to stop fermentation.

If desired, jet mixing can be utilized during fermentation, and if fermentation is conducted in the same vessel as saccharification the same equipment can be utilized. However, in some embodiments jet mixing is not necessary. For example, if fermentation is conducted during transport the movement of the rail car or tanker truck may provide adequate agitation.

Mixing Feedstock, Enzyme and Liquid

Mixing Characteristics

Various types of mixing devices are described below, and other mixing devices may be used. Suitable mixers have in common that they produce high velocity circulating flow, for example flow in a toroidal or elliptical pattern. Generally, preferred mixers exhibit a high bulk flow rate. Preferred mixers provide this mixing action with relatively low energy consumption. It is also generally preferred that the mixer produce relatively low shear and avoid heating of the liquid medium, as shear and/or heat can deleteriously affect the saccharifying agent (or microorganism, e.g., in the case of fermentation). As will be discussed in detail below, some preferred mixers draw the mixture through an inlet into a mixing element, which may include a rotor or impeller, and then expel the mixture from the mixing element through an outlet nozzle. This circulating action, and the high velocity of the jet exiting the nozzle, assist in dispersing material that is floating on the surface of the liquid or material that has settled to the bottom of the tank, depending on the orientation of the mixing element. Mixing elements can be positioned in different orientations to disperse both floating and settling material, and the orientation of the mixing elements can in some cases be adjustable.

In some preferred mixing systems the velocity $v_o$ of the jet as it meets the ambient fluid is from about 2 to 300 m/s, e.g., about 5 to 150 m/s or about 10 to 100 m/s. The power consumption of the mixing system may be about 20 to 1000 KW, e.g., 30 to 570 KW or 50 to 500 KW, or 150 to 250 KW for a 100,000 L tank. It is generally preferred that the power usage be low for cost-effectiveness.

Jet Mixing

Figure 22:
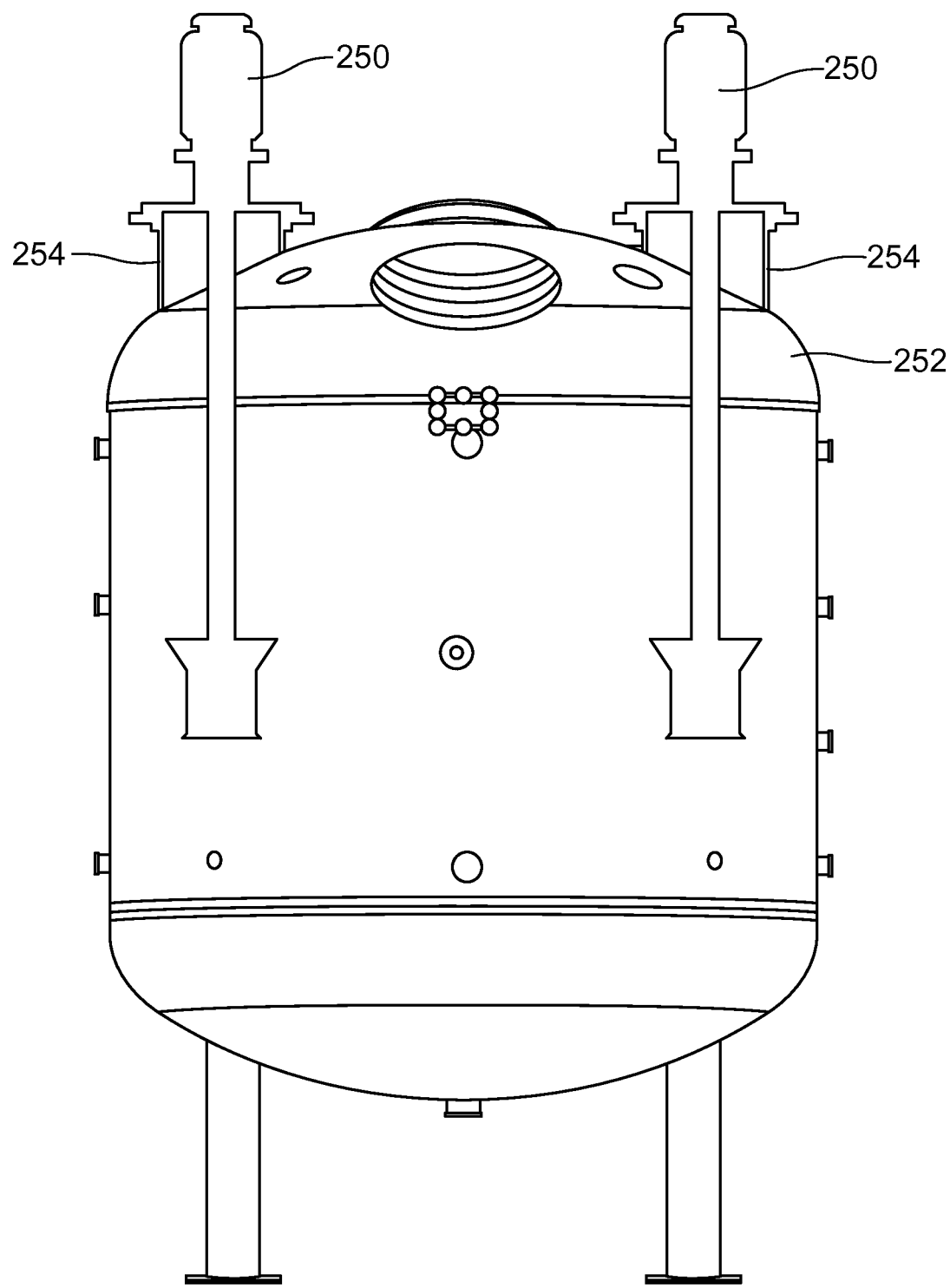
FIG. 22 is a cross-sectional view of a tank having a domed bottom and two jet mixers extending into the tank from above.

Jet mixing involves the discharge of a submerged jet, or a number of submerged jets, of high velocity liquid into a fluid medium, in this case the mixture of biomass feedstock, liquid medium and saccharifying agent. The jet of liquid penetrates the fluid medium, with its energy being dissipated by turbulence and some initial heat. This turbulence is associated with velocity gradients (fluid shear). The surrounding fluid is accelerated and entrained into the jet flow, with this secondary entrained flow increasing as the distance from the jet nozzle increases. The momentum of the secondary flow remains generally constant as the jet expands, as long as the flow does not hit a wall, floor or other obstacle. The longer the flow continues before it hits any obstacle, the more liquid is entrained into the secondary flow, increasing the bulk flow in the tank or vessel. When it encounters an obstacle, the secondary flow will lose momentum, more or less depending on the geometry of the tank, e.g., the angle at which the flow impinges on the obstacle. It is generally desirable to orient the jets and/or design the tank so that hydraulic losses to the tank walls are minimized. For example, it may be desirable for the tank to have an arcuate bottom (e.g., a domed headplate), and for the jet mixers to be oriented relatively close to the sidewalls, as shown in FIG. 22. The tank bottom (lower head plate) may have any desired domed configuration, or may have an elliptical or conical geometry.

Jet mixing differs from most types of liquid/liquid and liquid/solid mixing in that the driving force is hydraulic rather than mechanical. Instead of shearing fluid and propelling it around the mixing vessel, as a mechanical agitator does, a jet mixer forces fluid through one or more nozzles within the tank, creating high-velocity jets that entrain other fluid. The result is shear (fluid against fluid) and circulation, which mix the tank contents efficiently.

Figure 4:
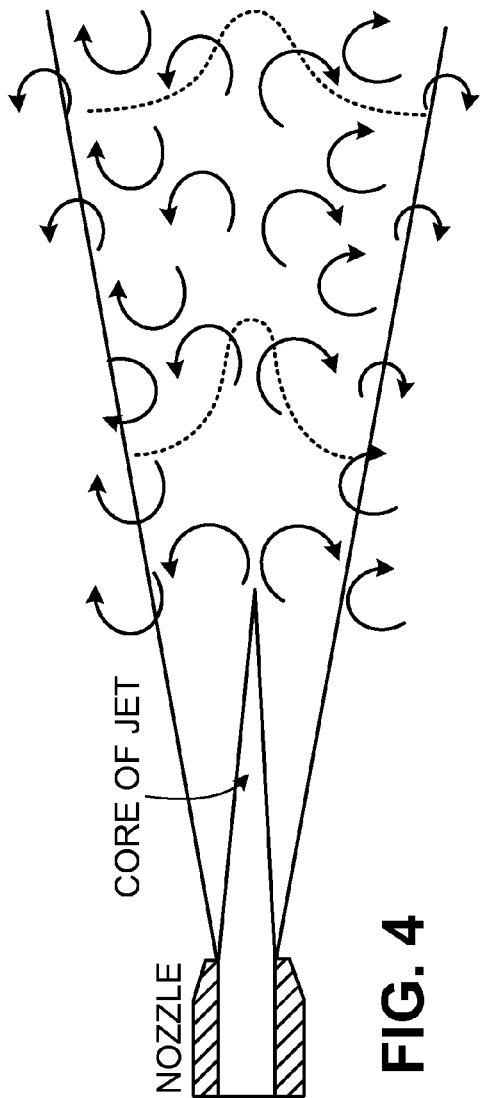
FIGS. 4 and 4A are diagrams illustrating jet flow exiting a nozzle.
Figure 4A:
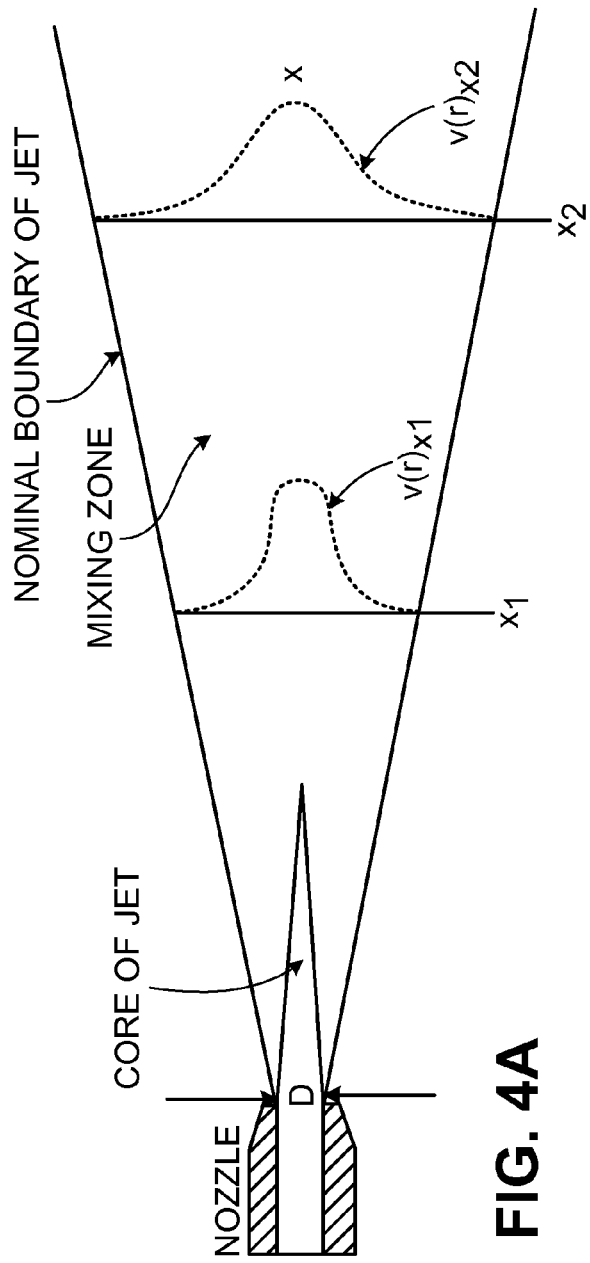
Figure 5:
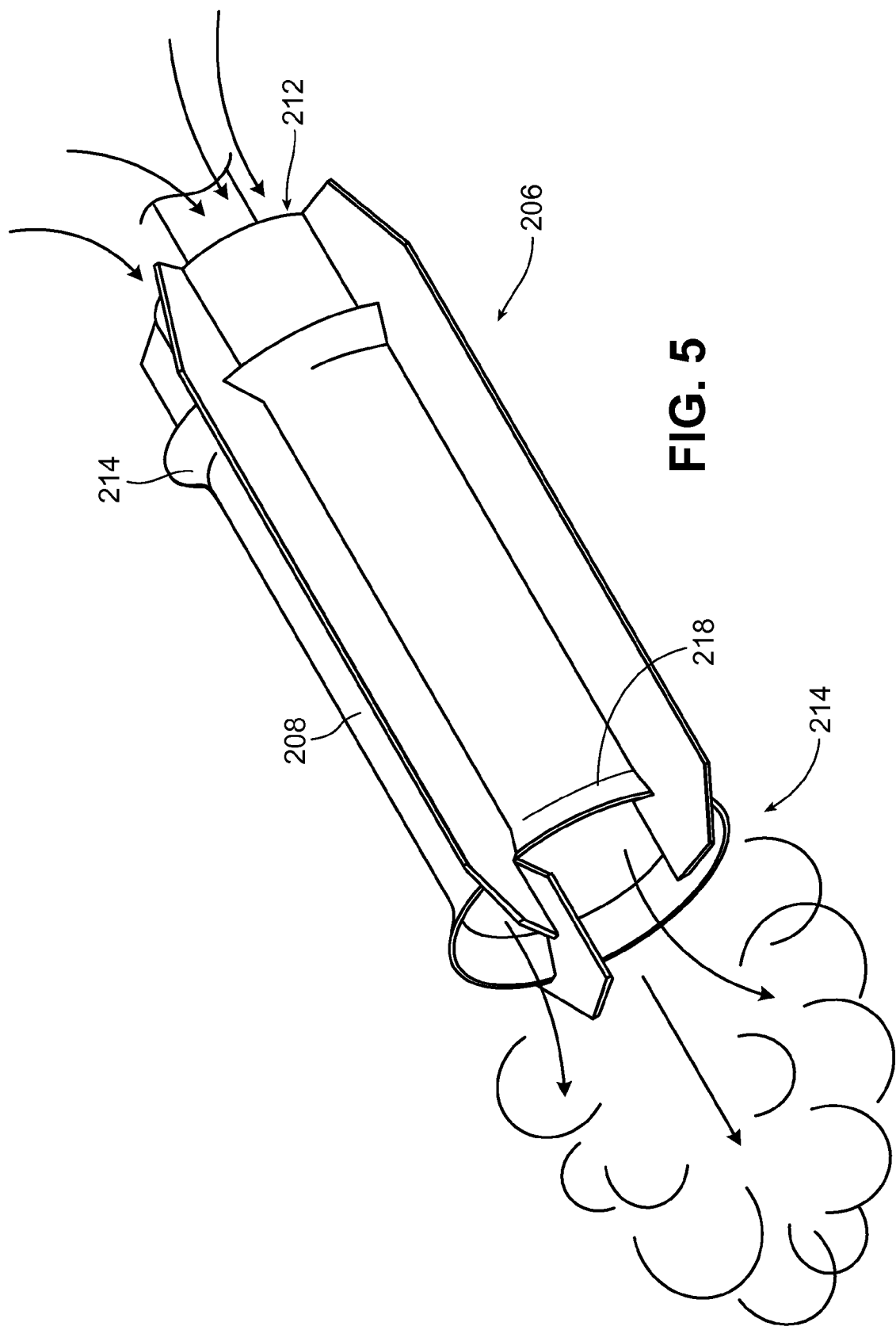
FIG. 5 is a diagrammatic perspective view of a jet-flow agitator according to one embodiment.
Figure 5A:
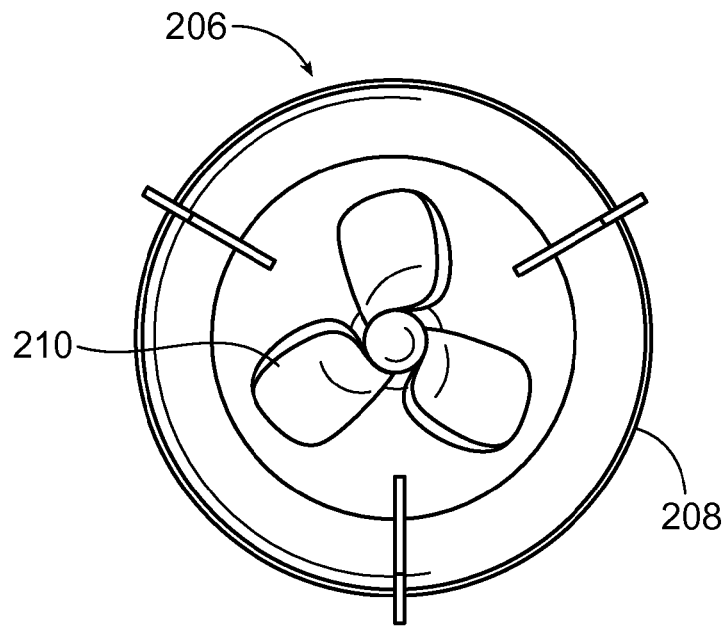
FIG. 5A is an enlarged perspective view of the impeller and jet tube of the jet-flow agitator of FIG. 5.
Figure 5B:
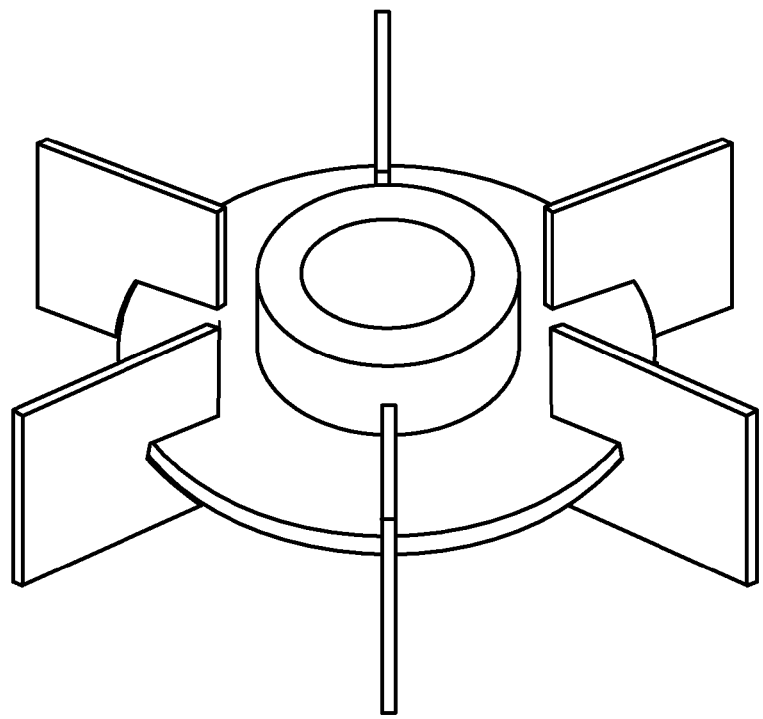
FIG. 5B is an enlarged perspective view of an alternate impeller.

Referring to FIG. 4, the high velocity gradient between the core flow from a submerged jet and the surrounding fluid causes eddies. FIG. 4A illustrates the general characteristics of a submerged jet. As the submerged jet expands into the surrounding ambient environment the velocity profile flattens as the distance (x) from the nozzle increases. Also, the velocity gradient dv/dr changes with r (the distance from the centerline of the jet) at a given distance x, such that eddies are created which define the mixing zone (the conical expansion from the nozzle).

In an experimental study of a submerged jet in air (the results of which are applicable to any fluid, including water), Albertson et al. ("Diffusion of Submerged Jets," Paper 2409, Amer. Soc. of Civil Engineers Transactions, Vol. 115:639-697, 1950, at p. 657) developed dimensionless relationships for $v(x)_{r=0}/v_o$ (centerline velocity), $v(r)_x/v(x)_{r=0}$ (velocity profile at a given x), $Q_x/Q_o$ (flow entrainment), and $E_x/E_o$ (energy change with x):

(1) Centerline velocity, $v(x)_{r=0}/v_o$:

$$\frac{v(r=0)}{v_o} \frac{x}{D_o} = 6.2$$

(2) velocity profile at any x, $v(r)_x/v(x)_{r=0}$:

$$\log\left[\frac{v(r)_x}{v_o}\frac{x}{D}\right] = 0.79 - 33\frac{r^2}{x^2}$$

(3) Flow and energy at any x:

$$\frac{Q_x}{Q_o} = 0.32\frac{x}{D_o} \quad (10.21)$$

$$\frac{E_x}{Q_o} = 4.1\frac{D_o}{x} \quad (10.22)$$

where:
v(r=0)=centerline velocity of submerged jet (m/s),
$v_o$=velocity of jet as it emerges from the nozzle (m/s),
x=distance from nozzle (m),
r=distance from centerline of jet (m),
$D_o$=diameter of nozzle (m),
$Q_x$=flow of fluid across any given plane at distance x from the nozzle (m3/s),
$Q_o$=flow of fluid emerging from the nozzle (m3/s),
E=energy flux of fluid across any given plane at distance x from the nozzle (m$^3$/s),
$E_o$=energy flux of fluid emerging from the nozzle (m$^3$/s).
("Water Treatment Unit Processes: Physical and Chemical," David W. Hendricks, CRC Press 2006, p. 411.)

Jet mixing is particularly cost-effective in large-volume (over 1,000 gal) and low-viscosity (under 1,000 cPs) applications. It is also generally advantageous that in most cases the pump or motor of the jet mixer not be submerged, e.g., when a pump is used it is generally located outside the vessel.

One advantage of jet mixing is that the temperature of the ambient fluid (other than directly adjacent the exit of the nozzle, where there may be some localized heating) is increased only slightly if at all. For example, the temperature may be increased by less than 5° C., less than 1° C., or not to any measurable extent.

Jet-Flow Agitators

One type of jet-flow agitator is shown in FIGS. 4-4A. This type of mixer is available commercially, e.g., from IKA under the tradename ROTOTRON™. Referring to FIG. 4, the mixer 200 includes a motor 202, which rotates a drive shaft 204. A mixing element 206 is mounted at the end of the drive shaft 204. As shown in FIG. 4A, the mixing element 206 includes a shroud 208 and, within the shroud, an impeller 210. As indicated by the arrows, when the impeller is rotated in its "forward" direction, the impeller 210 draws liquid in through the open upper end 212 of the shroud and forces the liquid out through the open lower end 214. Liquid exiting end 214 is in the form of a high velocity stream or jet. If the direction of rotation of the impeller 210 is reversed, liquid can be drawn in through the lower end 214 and ejected through the upper end 212. This can be used, for example, to suck in solids that are floating near or on the surface of the liquid in a tank or vessel. (It is noted that "upper" and "lower" refer to the orientation of the mixer in FIG. 4; the mixer may be oriented in a tank so that the upper end is below the lower end.)

The shroud 208 includes flared areas 216 and 218 adjacent its ends. These flared areas are believed to contribute to the generally toroidal flow that is observed with this type of mixer. The geometry of the shroud and impeller also concentrate the flow into a high velocity stream using relatively low power consumption.

Preferably, the clearance between the shroud 208 and the impeller 210 is sufficient so as to avoid excessive milling of the material as it passes through the shroud. For example, the clearance may be at least 10 times the average particle size of the solids in the mixture, preferably at least 100 times.

In some implementations, the shaft 204 is configured to allow gas delivery through the shaft. For example, the shaft 204 may include a bore (not shown) through which gas is delivered, and one or more orifices through which gas exits into the mixture. The orifices may be within the shroud 208, to enhance mixing, and/or at other locations along the length of the shaft 204.

The impeller 210 may have any desired geometry that will draw liquid through the shroud at a high velocity. The impeller is preferably a marine impeller, as shown in FIG. 4A, but may have a different design, for example, a Rushton impeller as shown in FIG. 4B, or a modified Rushton impeller, e.g., tilted so as to provide some axial flow.

In order to generate the high velocity flow through the shroud, the motor 202 is preferably a high speed, high torque motor, e.g., capable of operating at 500 to 20,000 RPM, e.g., 3,000 to 10,000 RPM. However, the larger the mixer (e.g., the larger the shroud and/or the larger the motor) the lower the rotational speed can be. Thus, if a large mixer is used, such as a 5 hp, 10 hp, 20 hp, or 30 hp or greater, the motor may be designed to operate at lower rotational speeds, e.g., less than 2000 RPM, less than 1500 RPM, or even 500 RPM or less. For example, a mixer sized to mix a 10,000-20,000 liter tank may operate at speeds of 900 to 1,200 RPM. The torque of the motor is preferably self-adjusting, to maintain a relatively constant impeller speed as the mixing conditions change over time, e.g., due to saccharification of the solids.

Advantageously, the mixer can be oriented at any desired angle or location in the tank, to direct the jet flow in a desired direction. Moreover, as discussed above, depending on the direction of rotation of the impeller the mixer can be used to draw fluid from either end of the shroud.

In some implementations, two or more jet mixers are positioned in the vessel, with one or more being configured to jet fluid upward ("up pump") and one or more being configured to jet fluid downward ("down pump"). In some cases, an up pumping mixer will be positioned adjacent a down pumping mixer, to enhance the turbulent flow created by the mixers. If desired, one or more mixers may be switched between upward flow and downward flow during processing. It may be advantageous to switch all or most of the mixers to up pumping mode during initial dispersion of the feedstock in the liquid medium, particularly if the feedstock is dumped or blown onto the surface of the liquid, as up pumping creates significant turbulence at the surface. Up pumping can also be used during fermentation to help remove $CO_2$ from the liquid by causing the gas to bubble to the surface where it can be vented.

Suction Chamber Jet Mixers

Another type of jet mixer includes a primary nozzle that delivers a pressurized fluid from a pump, a suction inlet adjacent the primary nozzle through which ambient fluid is drawn by the pressure drop between the primary nozzle and the wider inlet, and a suction chamber extending between the suction inlet and a secondary nozzle. A jet of high velocity fluid exits the secondary nozzle.

Figure 6:
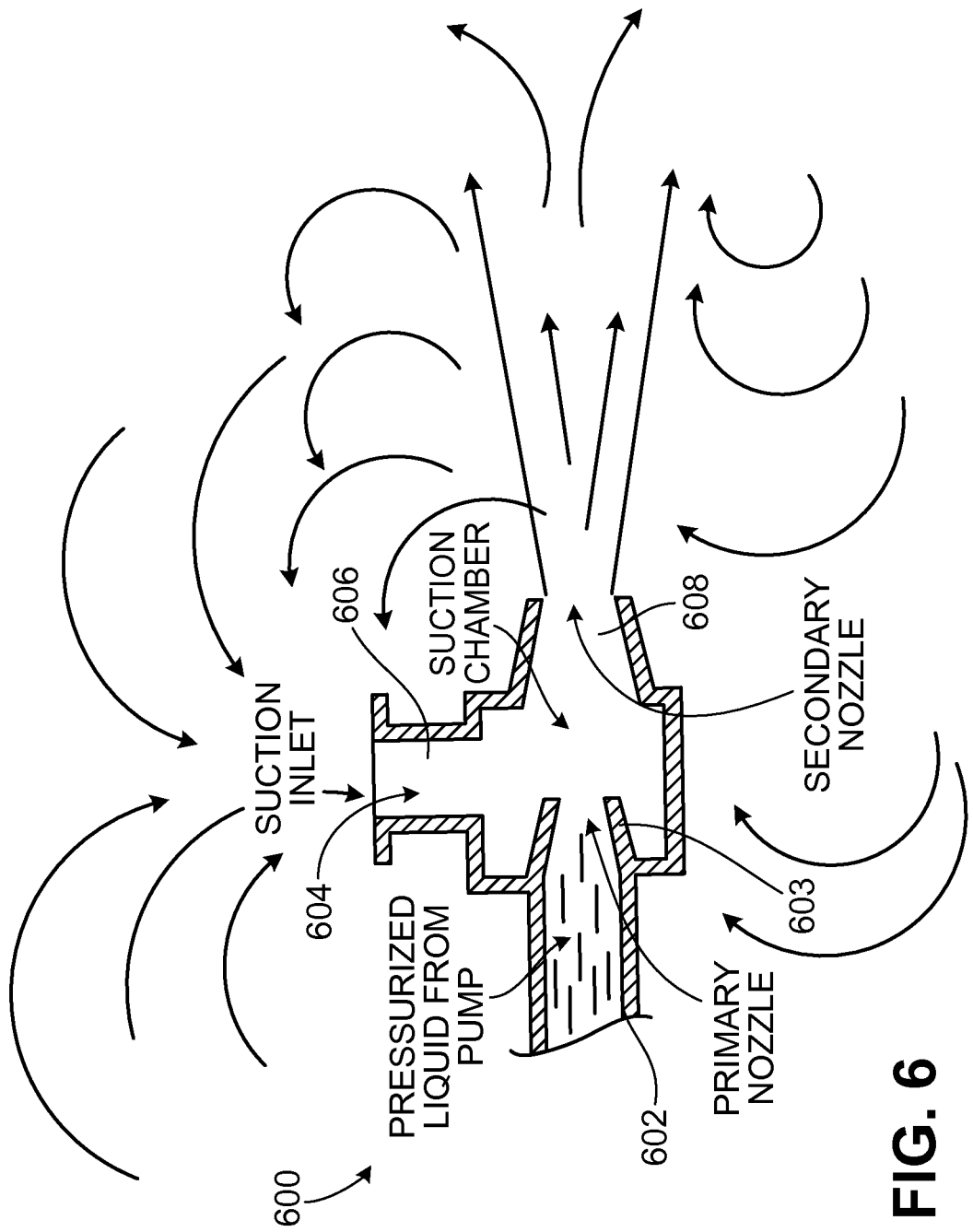
FIG. 6 is a diagram of a suction chamber jet mixing nozzle according to one embodiment.

An example of this type of mixer is shown in FIG. 6. As shown, in mixer 600 pressurized liquid from a pump (not shown) flows through an inlet passage 602 and exits through a primary nozzle 603. Ambient liquid is drawn through a suction inlet 604 into suction chamber 606 by the pressure drop caused by the flow of pressurized liquid. The combined flow exits from the suction chamber into the ambient liquid at high velocity through secondary nozzle 608. Mixing occurs both in the suction chamber and in the ambient liquid due to the jet action of the exiting jet of liquid.

Figure 6A:
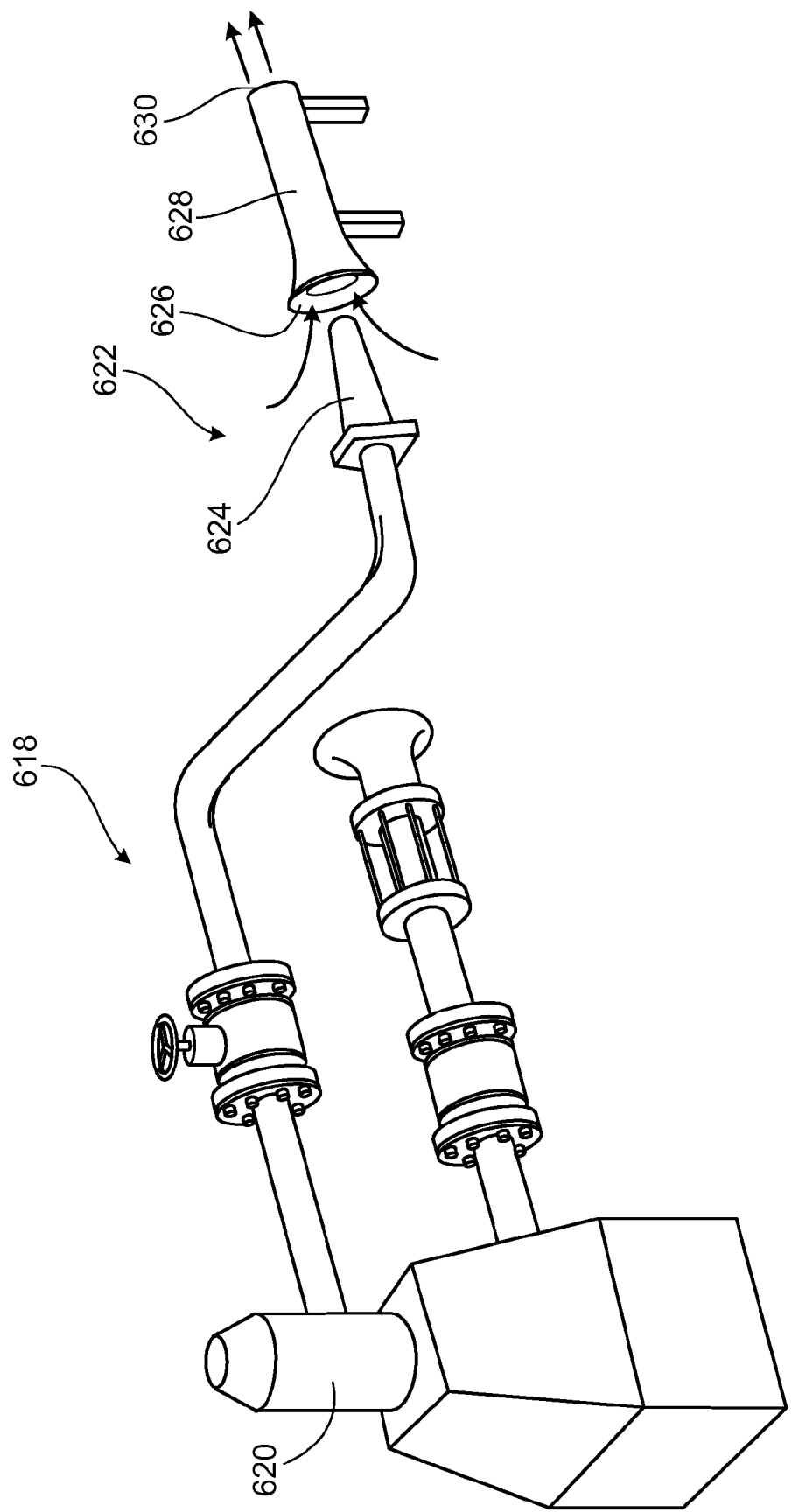
FIG. 6A is a perspective view of a suction chamber jet mixing system according to another embodiment.

A mixing system that operates according to a similar principle is shown in FIG. 6A. Mixers embodying this design are commercially available from ITT Water and Wastewater, under the tradename Flygt™ jet mixers. In system 618, pump 620 generates a primary flow that is delivered to the tank (not shown) through a suction nozzle system 622. The suction nozzle system 622 includes a primary nozzle 624 which functions in a manner similar to primary nozzle 603 described above, causing ambient fluid to be drawn into the adjacent open end 626 of ejector tube 628 due to the pressure drop induced by the fluid exiting the primary nozzle. The combined flow then exits the other end 630 of ejector tube 628, which functions as a secondary nozzle, as a high velocity jet.

Figure 7:
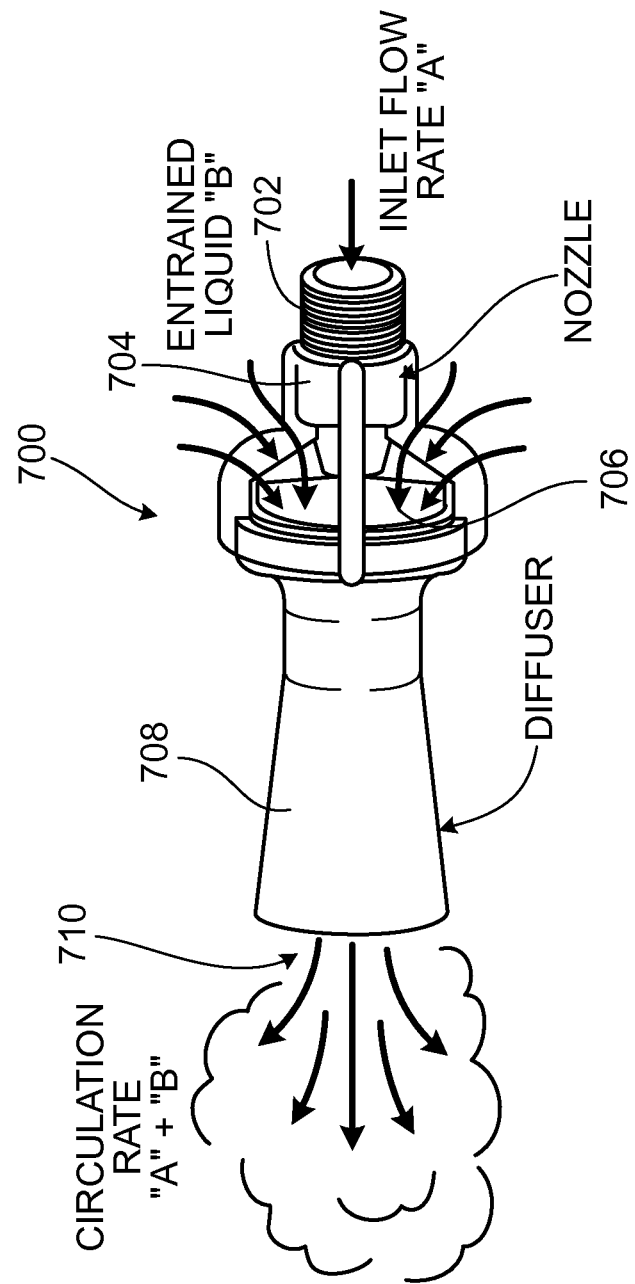
FIG. 7 is a diagrammatic perspective view of a jet mixing nozzle for a suction chamber jet mixing system according to another alternate embodiment.

The nozzle shown in FIG. 7, referred to as an eductor nozzle, operates under a similar principle. A nozzle embodying this design is commercially available under the tradename TeeJet®. As shown, in nozzle 700 pressurized liquid flows in through an inlet 702 and exits a primary nozzle 704, drawing ambient fluid in to the open end 706 of a diffuser 708. The combined flow exits the opposite open end 710 of the diffuser at a circulation flow rate A+B that is the sum of the inlet flow rate A and the flow rate B of the entrained ambient fluid.

Jet Aeration Type Mixers

Another type of jet mixing system that can be utilized is referred to in the wastewater industry as "jet aeration mixing." In the wastewater industry, these mixers are typically used to deliver a jet of a pressurized air and liquid mixture, to provide aeration. However, in the present application in some cases the jet aeration type mixers are utilized without pressurized gas, as will be discussed below. The principles of operation of jet aeration mixers will be initially described in the context of their use with pressurized gas, for clarity.

Figure 8A:
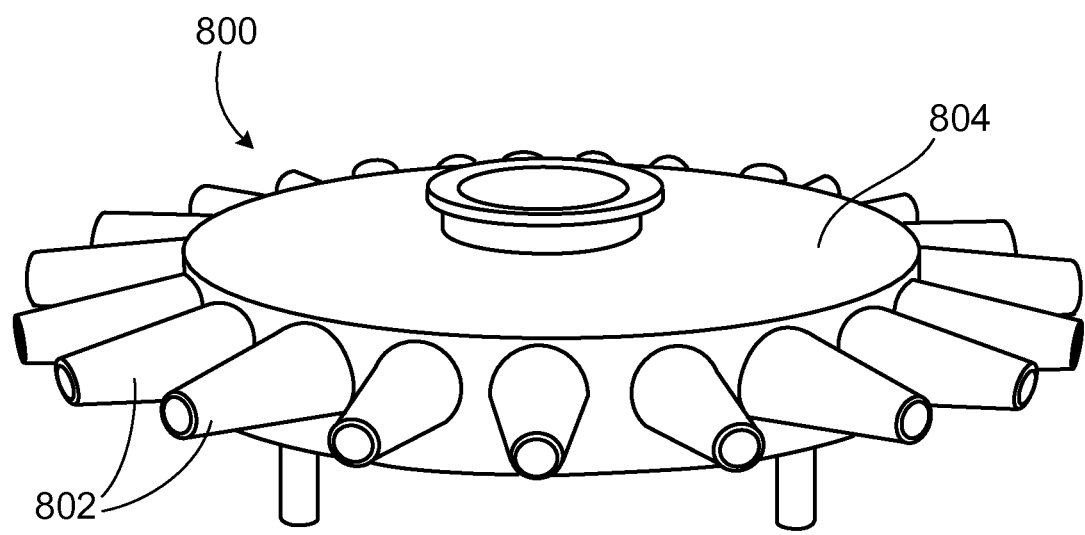
FIG. 8A is a perspective view of the jet mixer used in the jet aeration system of FIG. 8.
Figure 8B:
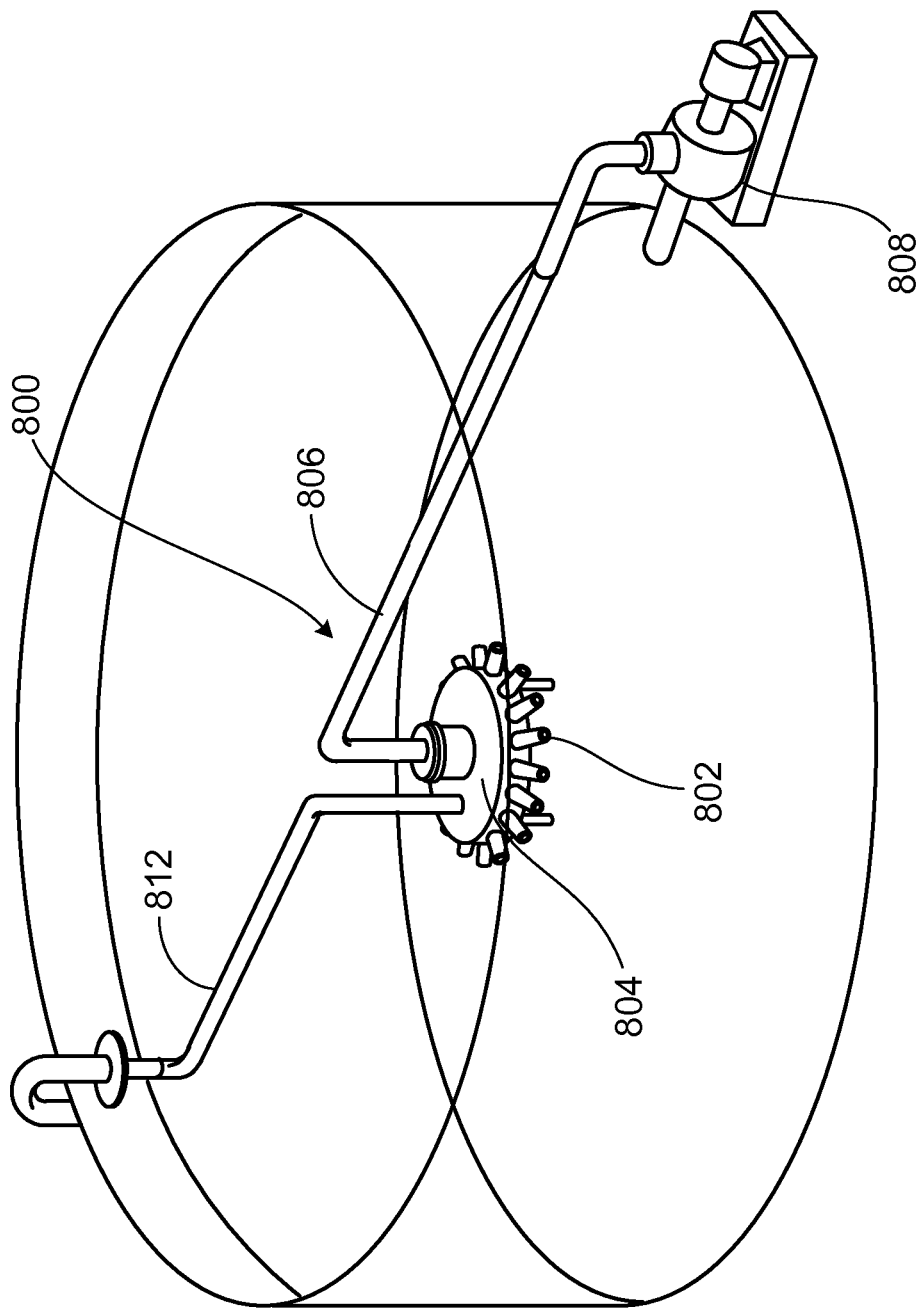
FIG. 8B is a diagrammatic perspective view of a similar system in which an air intake is provided.

An eddy jet mixer, such as the mixer 800 shown in FIGS. 8-8B, includes multiple jets 802 mounted in a radial pattern on a central hub 804. The radial pattern of the jets uniformly distributes mixing energy throughout the tank. The eddy jet mixer may be centrally positioned in a tank, as shown, to provide toroidal flow about the center axis of the tank. The eddy jet mixer may be mounted on piping 806, which supplies high velocity liquid to the eddy jet mixer. In the embodiment shown in FIG. 8B, air is also supplied to the eddy jet mixer through piping 812. The high velocity liquid is delivered by a pump 808 which is positioned outside of the tank and which draws liquid in through an inlet 810 in the side wall of the tank.

Figure 10:
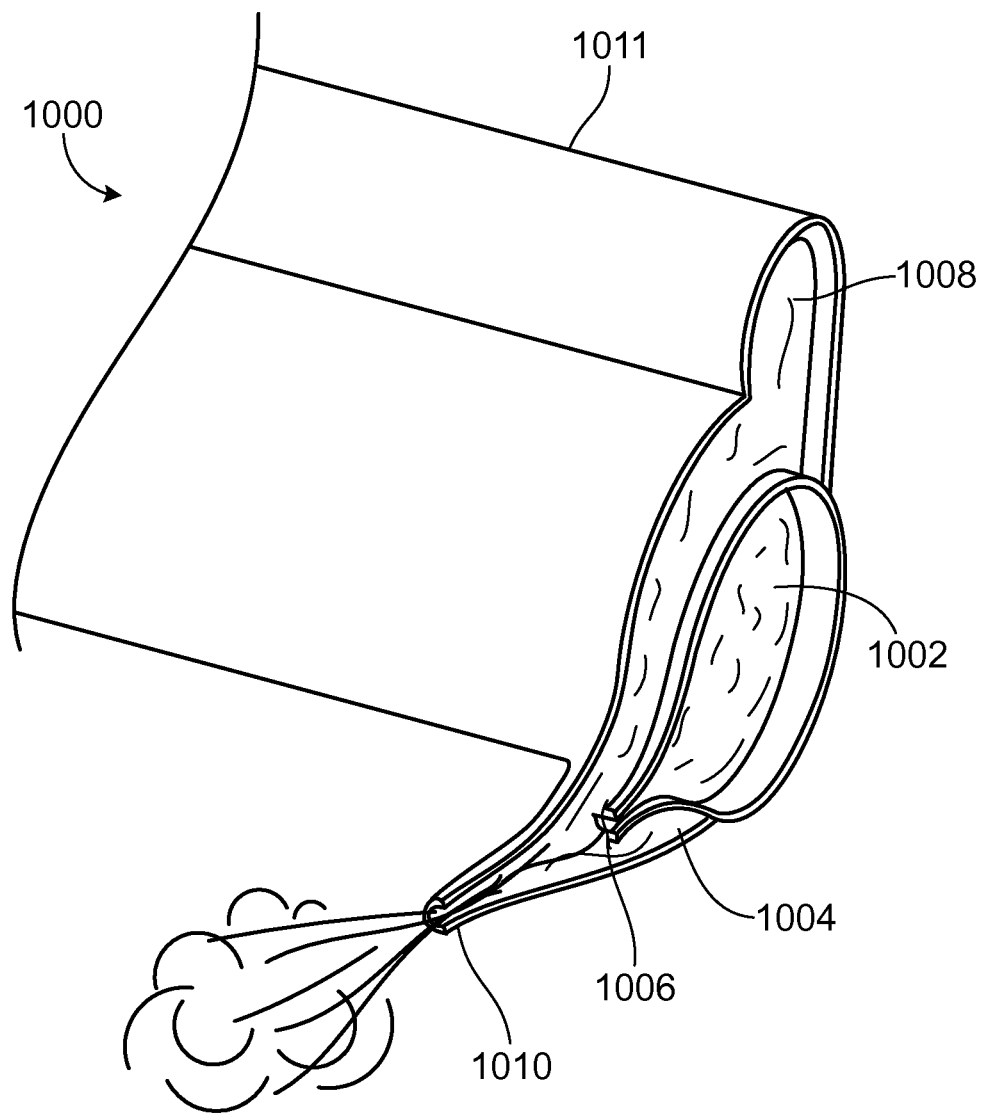
FIG. 10 is a cross-sectional view of a jet aeration type mixer according to an alternate embodiment.

FIGS. 9 and 10 show two types of nozzle configurations that are designed to mix a gas and a liquid stream and eject a high velocity jet. These nozzles are configured somewhat differently from the eddy jet mixer shown in FIGS. 8 and 8A but function in a similar manner. In the system 900 shown in FIG. 9, a primary or motive fluid is directed through a liquid line 902 to inner nozzles 904 through which the liquid travels at high velocity into a mixing area 906. A second fluid, e.g., a gas, such as compressed air, nitrogen or carbon dioxide, or a liquid, enters the mixing area through a second line 908 and entrained in the motive fluid entering the mixing area 906 through the inner nozzles. In some instances the second fluid is nitrogen or carbon dioxide so as to reduce oxidation of the enzyme. The combined flow from the two lines is jetted into the mixing tank through the outer nozzles 910. If the second fluid is a gas, tiny bubbles are entrained in the liquid in the mixture. Liquid is supplied to the liquid line 902 by a pump. Gas, if it is used, is provided by compressors. If a liquid is used as the second fluid, it can have the same velocity as the liquid entering through the liquid line 902, or a different velocity.

FIG. 10 shows an alternate nozzle design 1000, in which outer nozzles 1010 (of which only one is shown) are positioned along the length of an elongated member 1011 that includes a liquid line 1002 that is positioned parallel to a second line 1008. Each nozzle includes a single outer nozzle 1010 and a single inner nozzle 1004. Mixing of the motive liquid with the second fluid proceeds in the same manner as in the system 900 described above.

Figure 11:
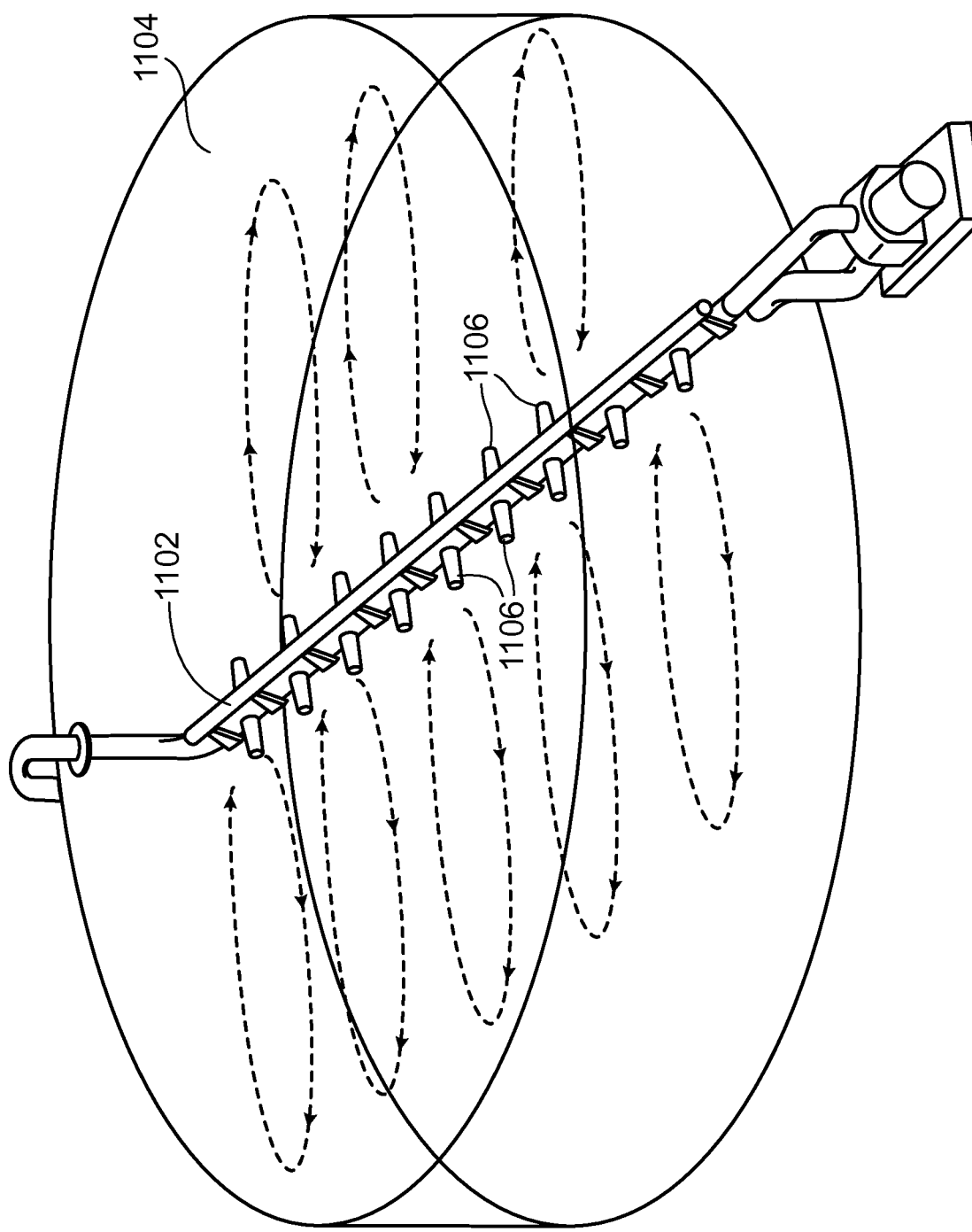
FIGS. 11-13 are diagrams illustrating alternative flow patterns in tanks containing different configurations of jet mixers.
Figure 12:
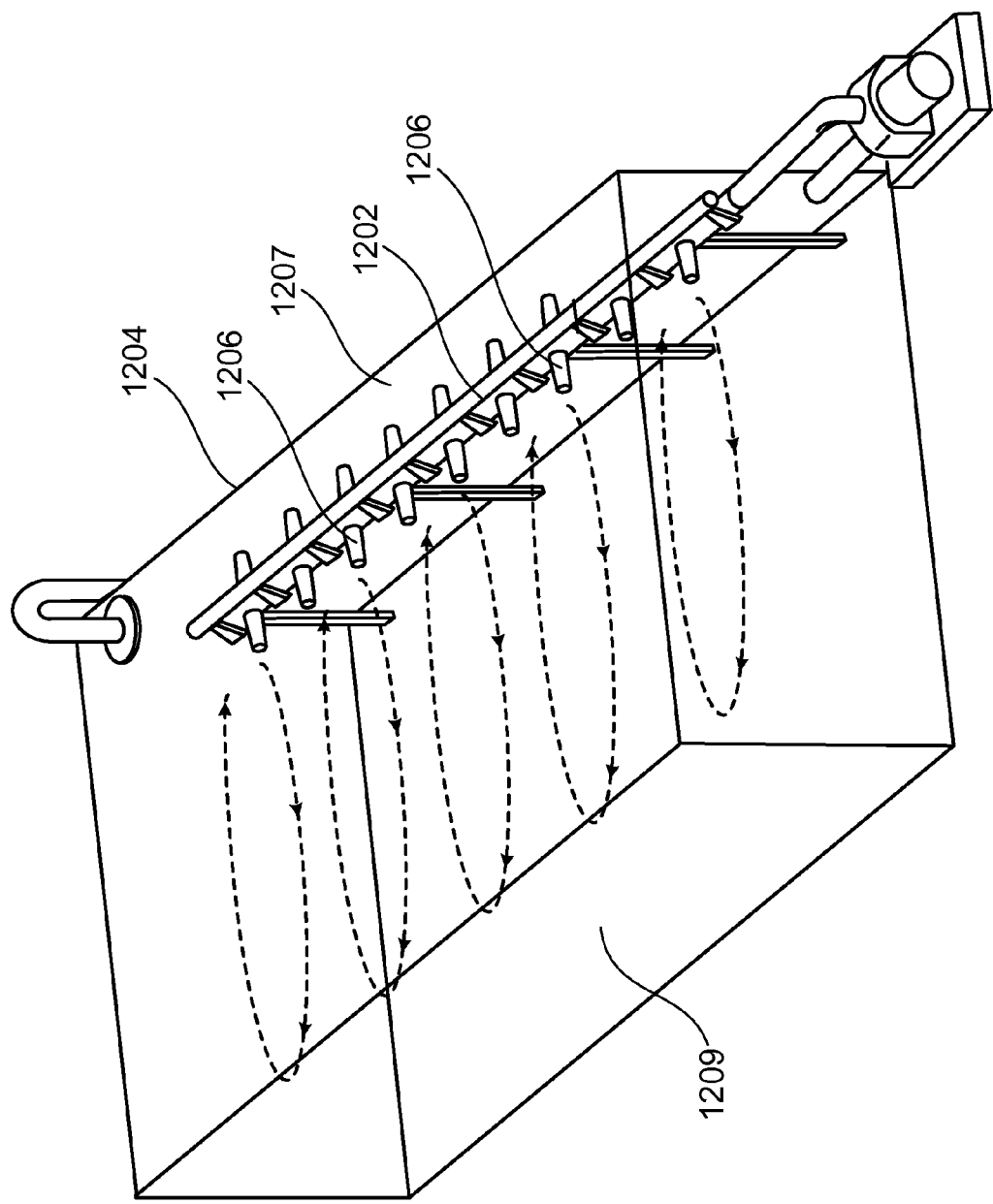

FIGS. 11 and 12 illustrate examples of jet aeration type mixing systems in which nozzles are positioned along the length of an elongated member. In the example shown in FIG. 11, the elongated member 1102 is positioned along the diameter of the tank 1104, and the nozzles 1106 extend in opposite directions from the nozzle to produce the indicated flow pattern which includes two areas of generally elliptical flow, one on either side of the central elongated member. In the example shown in FIG. 12, the tank 1204 is generally rectangular in cross section, and the elongated member 1202 extends along one side wall 1207 of the tank. In this case, the nozzles 1206 all face in the same direction, towards the opposite side wall 1209. This produces the flow pattern shown, in which flow in the tank is generally elliptical about a major axis extending generally centrally along the length of the tank. In the embodiment shown in FIG. 12, the nozzles may be canted towards the tank floor, e.g., at an angle of from about 15 to 30 degrees from the horizontal.

Figure 13:
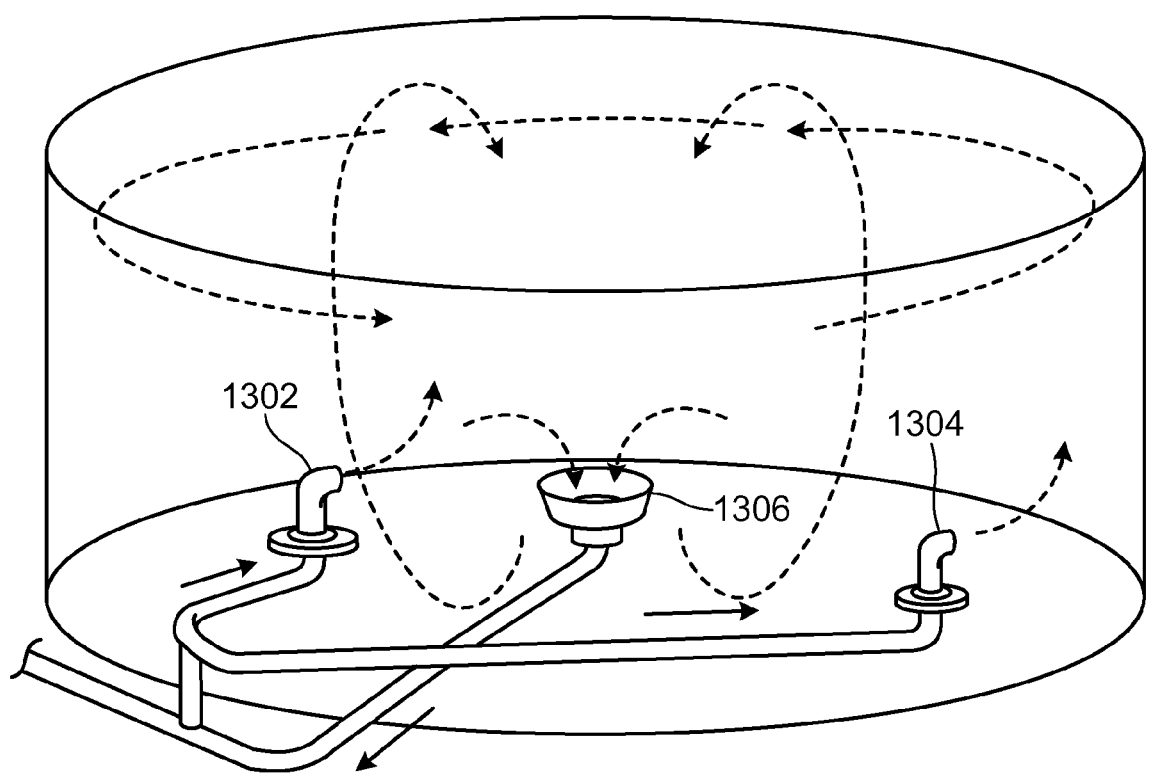

In another embodiment, shown in FIG. 13, the nozzles 1302, 1304, and suction inlet 1306 are arranged to cause the contents of the tank to both revolve and rotate in a toroidal, rolling donut configuration around a central vertical axis of the tank. Flow around the surface of the toroid is drawn down the tank center, along the floor, up the walls and back to the center, creating a rolling helix pattern, which sweeps the center and prevents solids from settling. The toroidal pattern is also effective in moving floating solids to the tank center where they are pulled to the bottom and become homogenous with the tank contents. The result is a continuous helical flow pattern, which minimizes tank dead spots.

Backflushing

Figure 14:
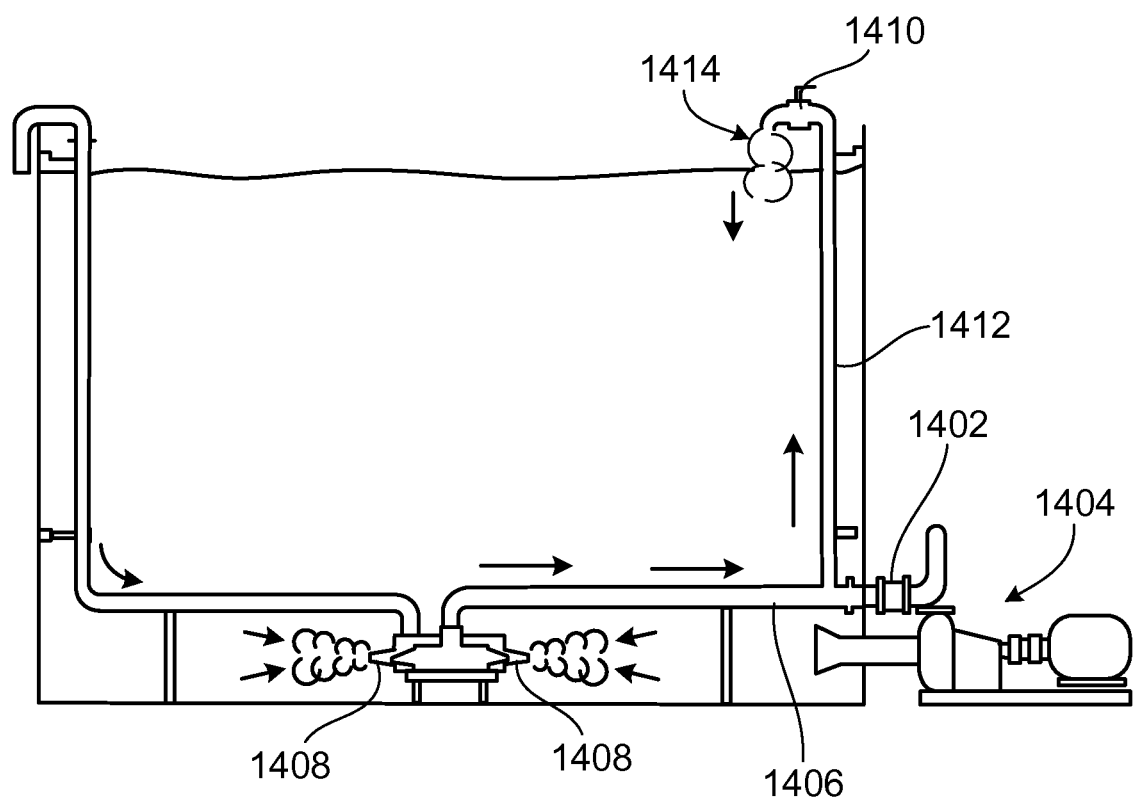
FIG. 14 is a diagram illustrating the flow pattern that occurs in a tank during backflushing according to one embodiment.

In some instances, the jet nozzles described herein can become plugged, which may cause efficiency and cost effectiveness to be reduced. Plugging of the nozzles may be removed by reversing flow of the motive liquid through the nozzle. For example, in the system shown in FIG. 14, this is accomplished by closing a valve 1402 between the pump 1404 and the liquid line 1406 flowing to the nozzles 1408, and activating a secondary pump 1410. Secondary pump 1410 draws fluid in through the nozzles. The fluid then travels up through vertical pipe 1412 due to valve 1402 being closed. The fluid exits the vertical pipe 1412 at its outlet 1414 for recirculation through the tank.

Mixing in Transit/Portable Mixers

Figure 15:
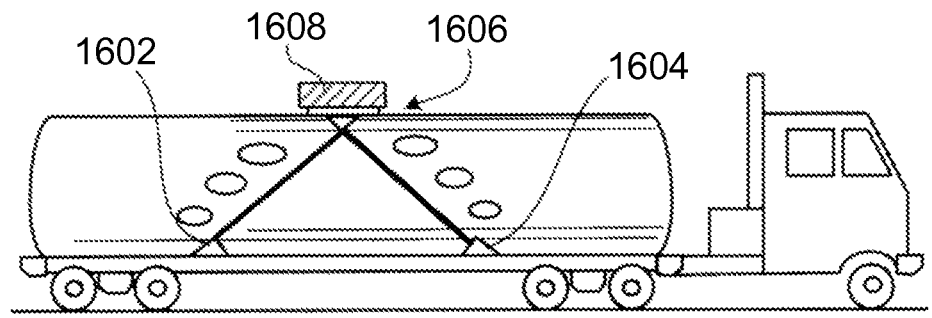
FIGS. 15 and 15A show a tanker truck and a rail car, respectively, set up for in-transit mixing using a pulsed air portable mixing system.
Figure 15A:
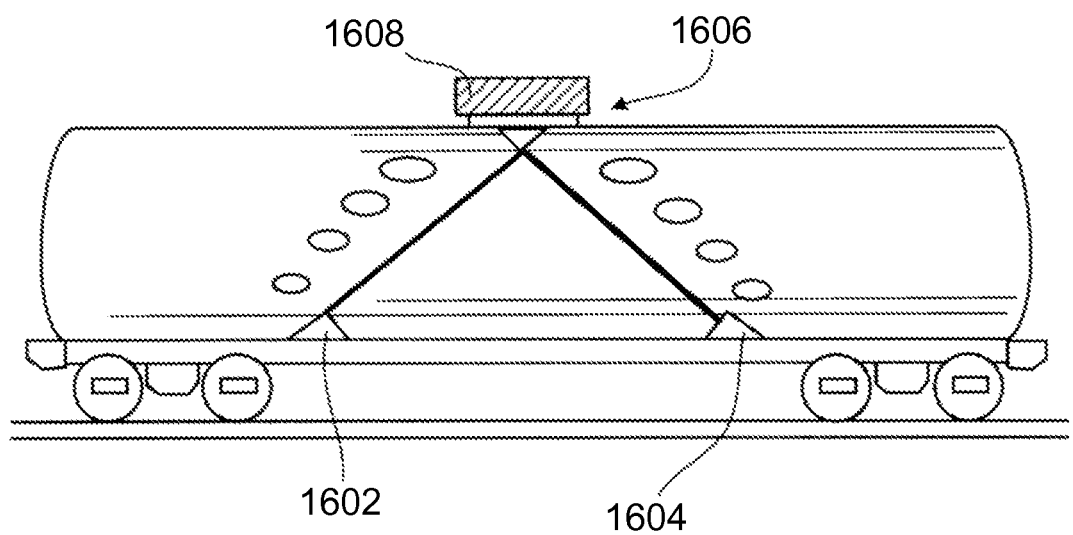

As noted above, if desired saccharification can take place in part or entirely during transportation of the mixture, e.g., between a first processing plant for treating the feedstock and a second processing plant for production of a final product such as ethanol. In this case, mixing can be conducted using a jet mixer designed for rail car or other portable use. Examples of such mixers will be discussed below. As shown diagrammatically in FIGS. 15 and 15A, mixers 1602, 1604 can be inserted through a port 1606 in a tank, e.g., of a truck (FIG. 15) or a railcar (FIG. 15A). The mixer can be operated using a control system 1608 external to the tank, which may include for example a motor and/or a supply or compressed air, depending on the type of mixing system used, and a controller configured to control the operation of the mixer. Venting (not shown) may also be provided.

Other Mixing Systems/Nozzles

Pulsed Air/Fluid

An alternative type of mixer utilizes a gas delivered in pulses to the mixture. Such a mixer is shown diagrammatically in FIGS. 15 and 15A, as an example of a portable railcar mixer. Metered amounts of high pressure gas are injected or pulsed under flat round discs (accumulator plates) positioned near the tank bottom. The sudden release of air shocks the liquid. As the gas moves outward between the plate and the tank floor, it sweeps out solids that have settled. The gas then accumulates above the plate into large, oval shaped bubbles. As each bubble rises to the surface, it pushes the liquid above it up and out towards the tank perimeter. The liquid moves toward the sides of the tank and travels down the tank wall to the bottom. This movement of the bubbles forces solids to the surface and creates a generally circular or toroidal circulation of liquid in the tank. The gas may be, for example, air, nitrogen, or carbon dioxide. The tank is vented (not shown) to allow gas to escape from the tank during mixing.

Low Speed Agitators

Figure 16:
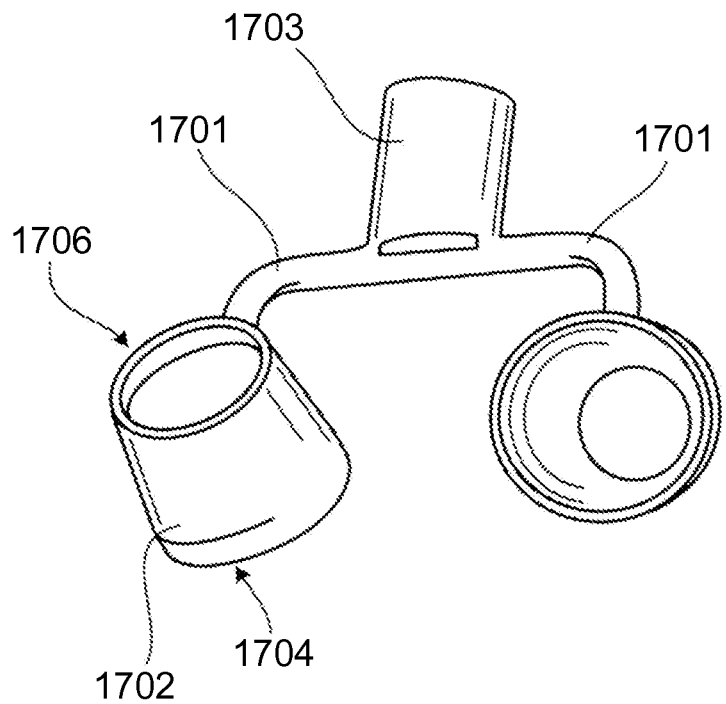
FIGS. 16 and 16A are perspective views of two embodiments of mixing heads used in a mixer according to an alternate embodiment.
Figure 16A:
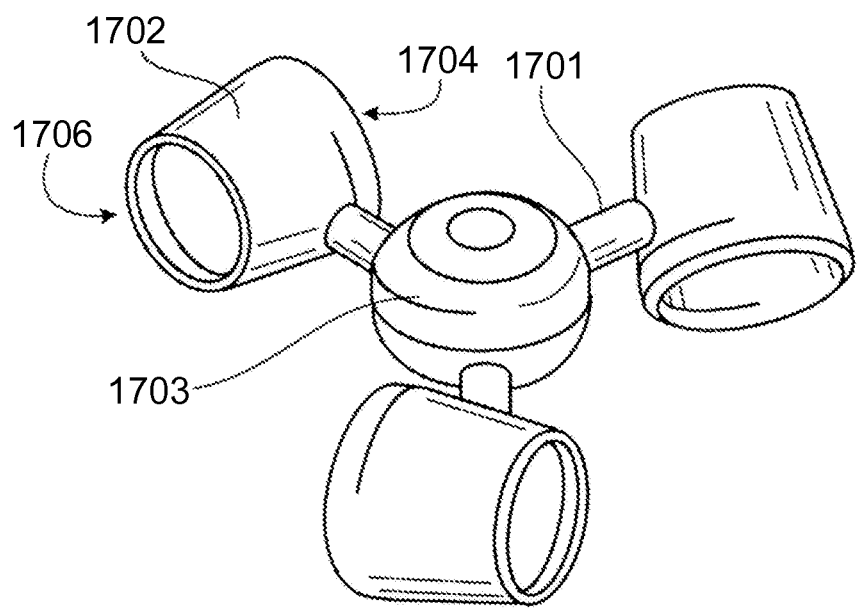
Figure 17:
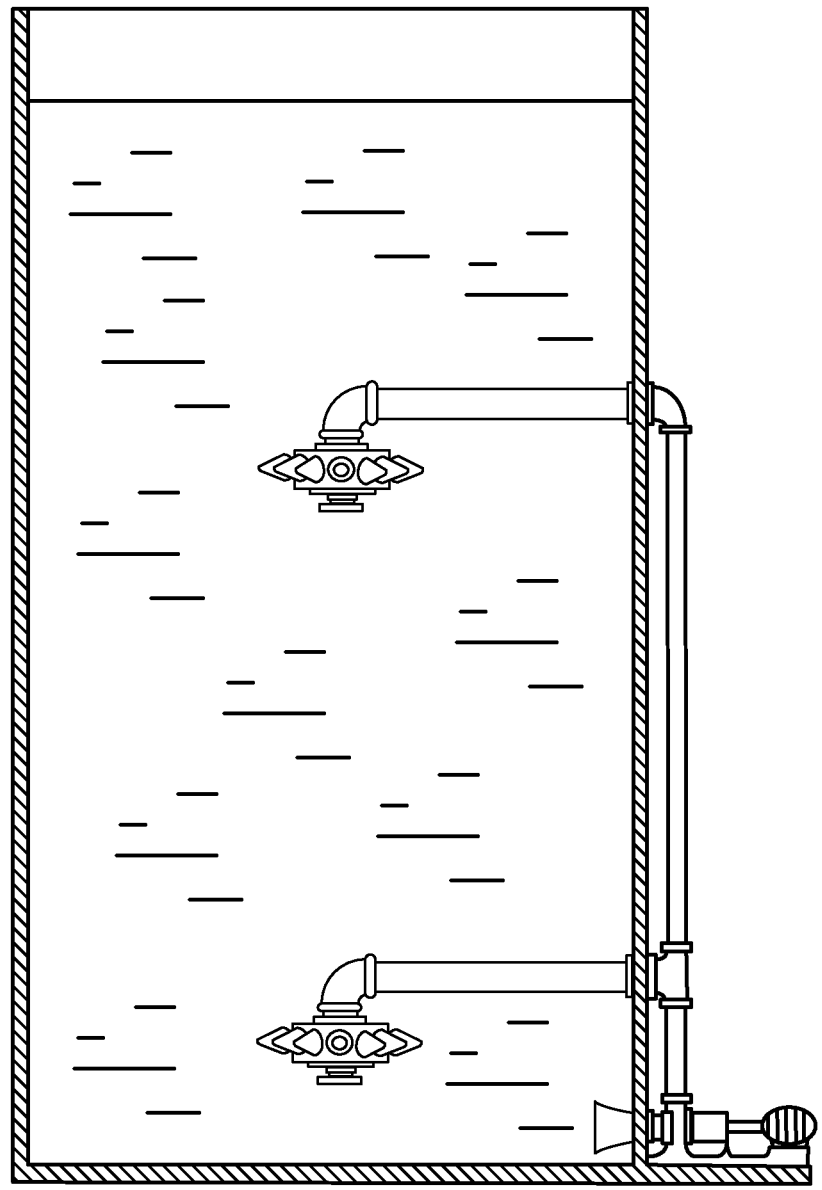
FIG. 17 is a side view of a jet aeration type system according to another embodiment, showing a multi-level arrangement of nozzles in a tank.

FIGS. 16 and 16A illustrate agitators configured to be mounted on a shaft (not shown) for rotational mixing at relatively low speeds. The agitators may include, for example, two mixing elements 1702 (FIG. 16), or three mixing elements (FIG. 16A), mounted on support arms 1701 about a central mounting hub 1703 that is disposed to receive a shaft.

The mixing elements 1702 are in the form of truncated cones, each of which has a first end 1704 and a second end 1706. The first end has a cross-section greater than the cross-section of the second end. The mixing elements are positioned such that the central axes of the mixing elements are disposed at an angle relative to a plane of rotation of the mixing elements.

The agitator is rotated in a direction so that liquid flows in through the first end 1704 and out through the second end 1706 at a higher velocity, creating dynamic flow conditions by generating turbulent flow at the tapered end of each mixing element. The angulation of the mixing elements relative to the plane of rotation tends to cause a continuous closed circular flow which in the vicinity of an adjacent tank or container wall flows upwardly and in the central part of the tank or container flows downwardly coaxially to the mixer shaft where it passes through the intermediate spaces between the support arms 1701. The intensity of this circular flow depends on the magnitude of the angle.

Mixers of this type are available commercially from Inotec under the tradename Visco-Jet™. Folding mixers are available which can be put in rail car or other transport container. A similar type of mixer is described in U.S. Pat. No. 6,921, 194, the full disclosure if which is incorporated herein by reference.

Minimizing Hold Up on Tank Walls

In some situations, in particular at solids levels approaching a theoretical or practical limit, material may accumulate along the side wall and/or bottom wall of the tank during mixing. This phenomenon, referred to as "hold up," is undesirable as it can result in inadequate mixing. Several approaches can be taken to minimize hold up and ensure good mixing throughout the tank.

Figure 18:
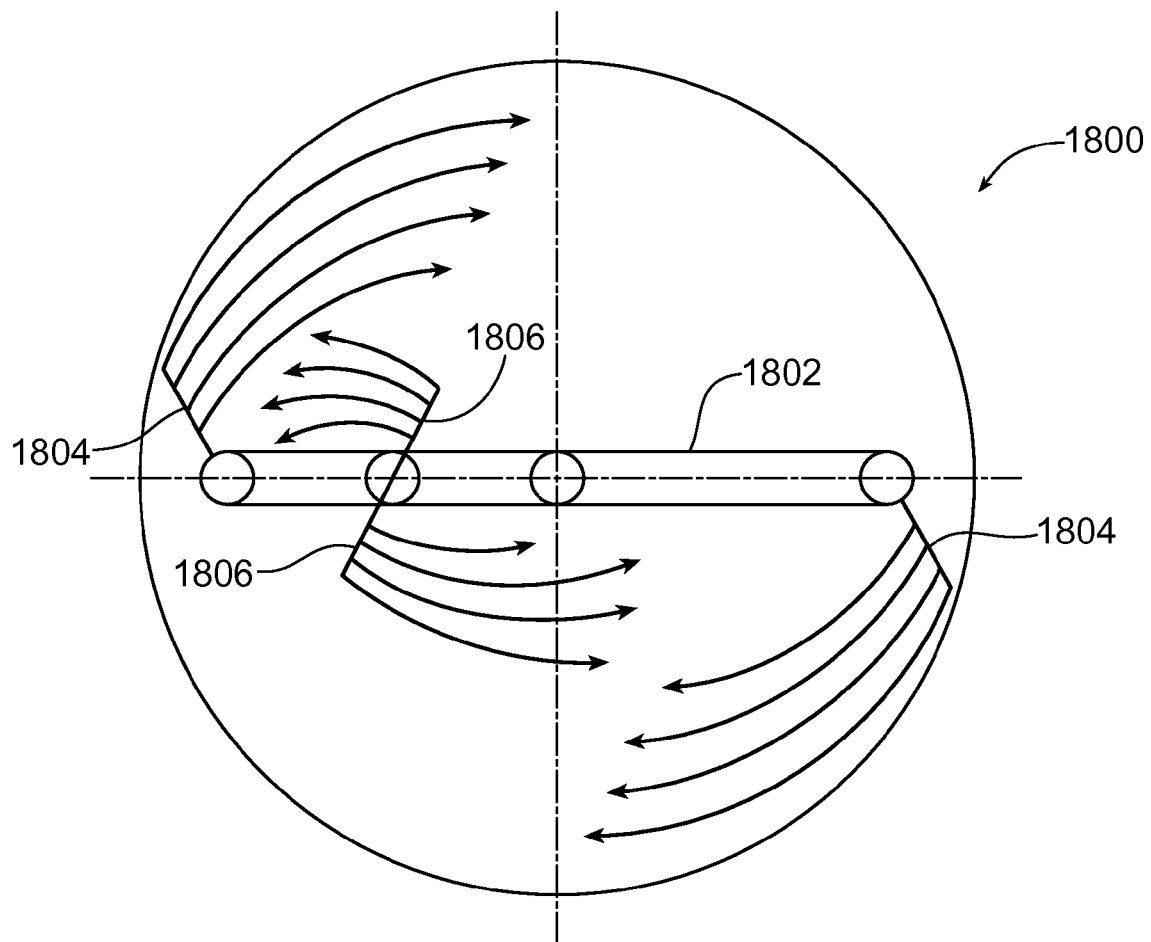
FIGS. 18 and 18A are a diagrammatic top view and a perspective view, respectively, of a device that minimizes hold up along the walls of a tank during mixing.
Figure 18A:
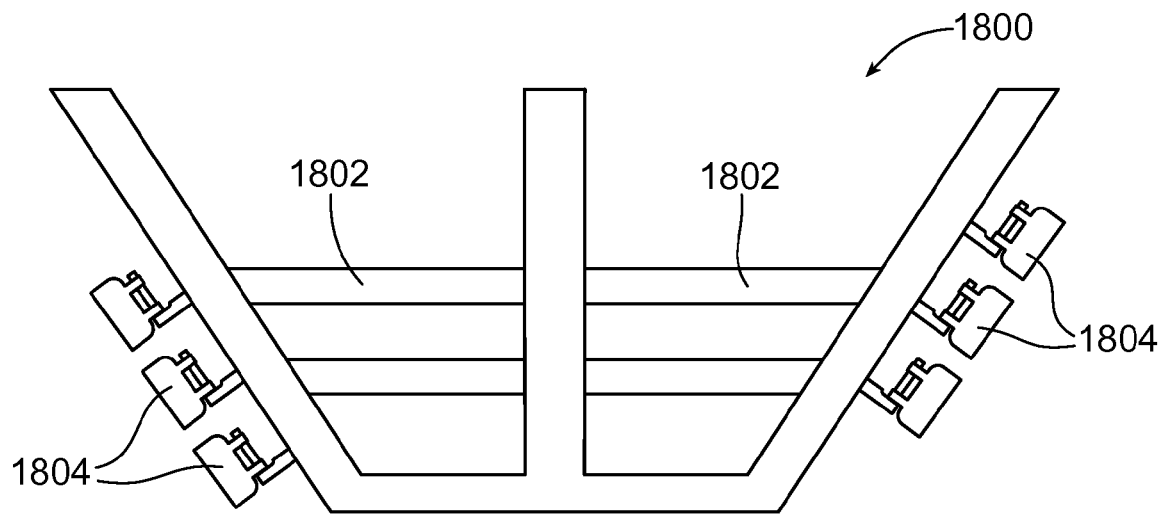

For example, in addition to the jet mixing device(s), the tank can be outfitted with a scraping device, for example a device having a blade that scrapes the side of the tank in a "squeegee" manner. Such devices are well known, for example in the dairy industry. Suitable agitators include the side and bottom sweep agitators and scraper blade agitators manufactured by Walker Engineered Products, New Lisbon, Wis. As shown in FIG. 18, a side and bottom sweep agitator 1800 may include a central elongated member 1802, mounted to rotate about the axis of the tank. Side wall scraper blades 1804 are mounted at each end of the elongated member 1802 and are disposed at an angle with respect to the elongated member. In the embodiment shown, a pair of bottom wall scraper blades 1806 are mounted at an intermediate point on the elongated member 1802, to scrape up any material accumulating on the tank bottom. These scrapers may be omitted if material is not accumulating on the tank bottom. As shown in FIG. 18A, the scraper blades 1804 may be in the form of a plurality of scraper elements positioned along the side wall. In other embodiments, the scraper blades are continuous, or may have any other desired geometry.

In other embodiments, the jet mixer itself is configured so as to minimize hold up. For example, the jet mixer may include one or more movable heads and/or flexible portions that move during mixing. For example, the jet mixer may include an elongated rotatable member having a plurality of jet nozzles along its length. The elongated member may be planar, as shown in FIG. 19, or have a non-planar shape, e.g., it may conform to the shape of the tank walls as shown in FIG. 20.

Figure 19:
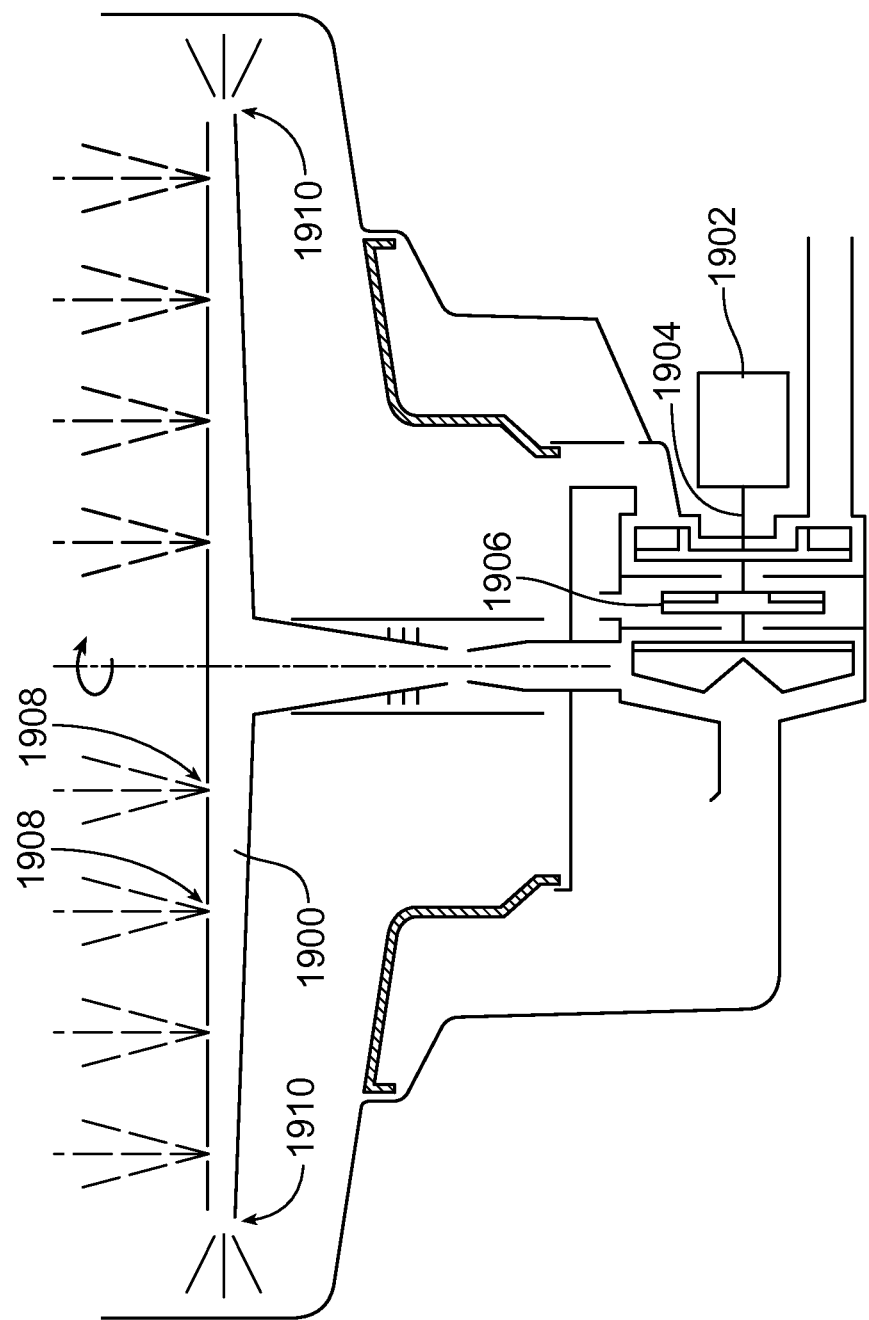
FIGS. 19, 20, and 21-21A are views of various water jet devices that provide mixing while also minimizing hold up along the tank walls.

Referring to FIG. 19, the jet mixer nozzles may be positioned on a rotating elongated member 1900 that is driven by a motor 1902 and shaft 1904. Water or other fluid is pumped through passageways in the rotating member, e.g., by a pump impeller 1906, and exits as a plurality of jets through jet orifices 1908 while the member 1900 rotates. To reduce hold up on the tank side walls, orifices 1910 may be provided at the ends of the member 1900.

Figure 20:
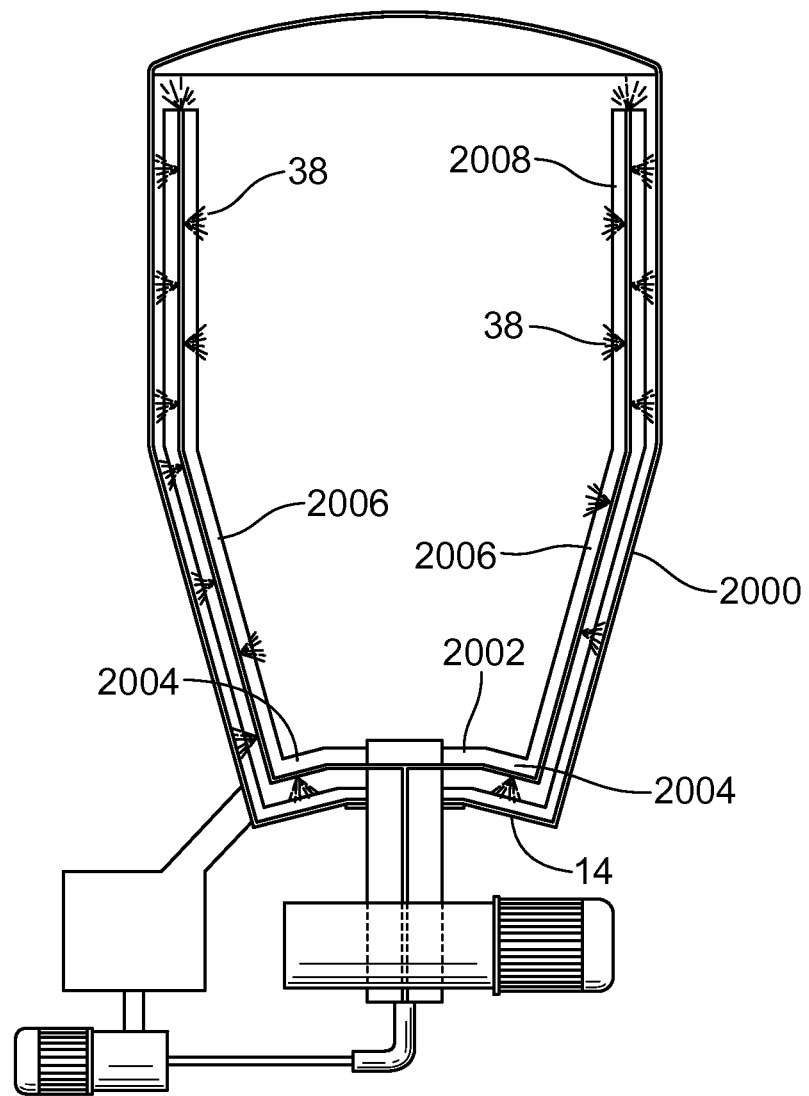

In the embodiment shown in FIG. 20, to conform to the particular shape of the tank 2000 the elongated member includes horizontally extending arms 2002, downwardly inclined portions 2004, outwardly and upwardly inclined portions 2006, and vertically extending portions 2008. Fluid is pumped through passageways within the elongated member to a plurality of jet orifices 38, through which jets are emitted while the elongated member is rotated.

In both of the embodiments shown in FIGS. 19 and 20, the jets provide mixing while also washing down the side walls of the tank.

Figure 21:
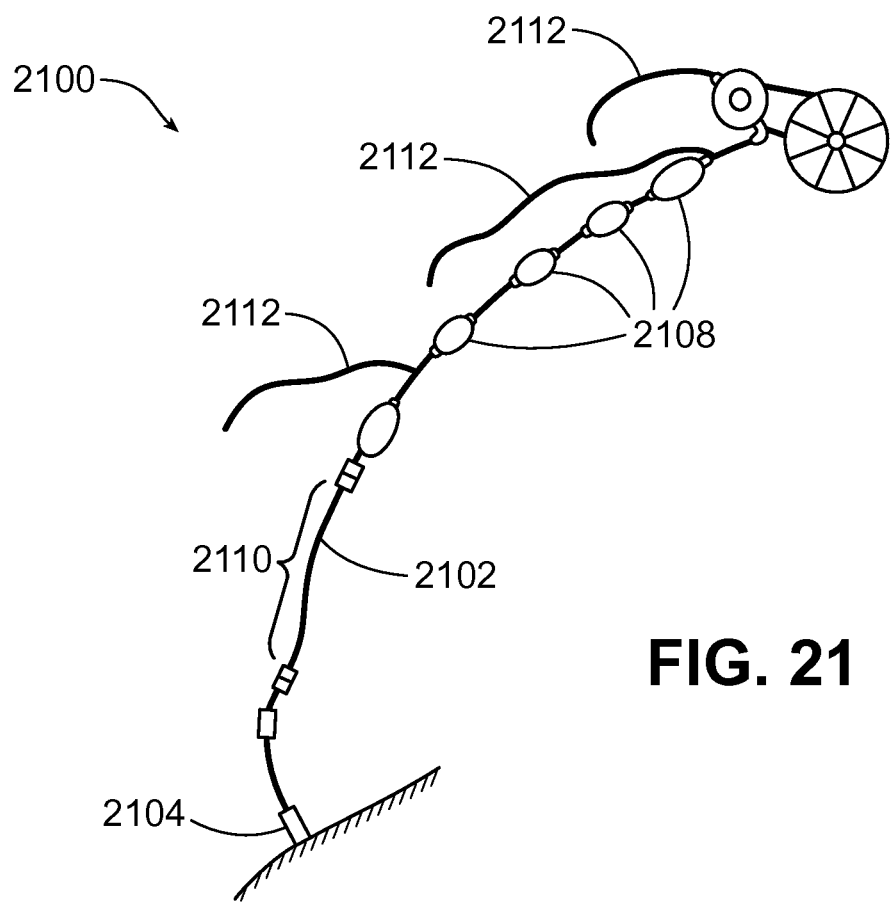
Figure 21A:
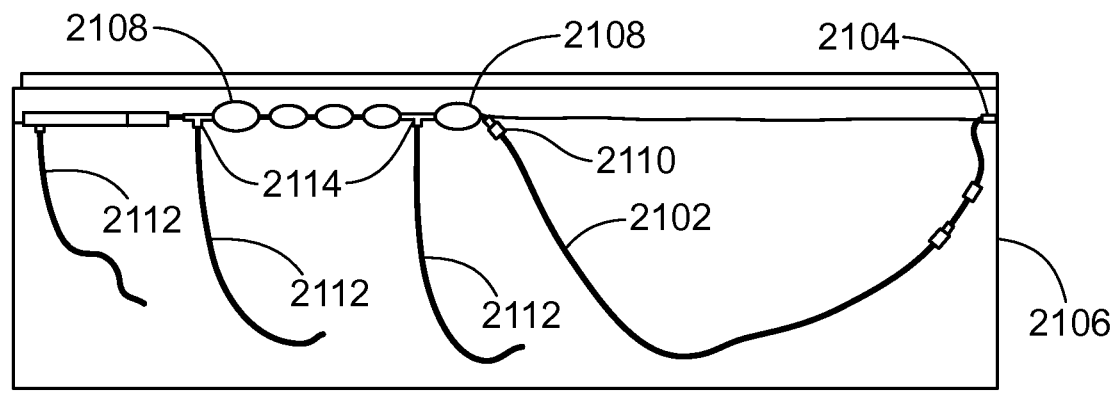

In other embodiments, the jet mixer may include flexible members and or adjustable members (e.g., bendable or telescoping tubes) through which the jets are delivered. For example, as shown diagrammatically in FIGS. 21 and 21A, the jet mixing device may be made up of flexible tubing, in the manner of a floating type of pool cleaner, such as is disclosed in U.S. Pat. No. 3,883,368. In the system 2100 shown, a flexible supply hose 2102 delivers fluid from an inlet 2104 in the sidewall of the tank 2106. The supply hose 2102 extends along the surface of the liquid in the tank via a series of buoys 2108 and swivels 2110. A plurality of flexible hoses 2112 are secured at their upper ends to spaced T-joints 2114 in the floating portion of the supply hose 2102. Fluid is jetted from the open distal ends of the flexible hoses 2112, resulting in mixing of the contents of the tank and removal of hold up on the tank side walls.

In some implementations, combinations of the embodiments described above may be used. For example, combinations of planar and non-planar rotating or oscillating elongated members may be used. The moving nozzle arrangements described above can be used in combination with each other and/or in combination with scrapers. A plurality of moving nozzle arrangements can be used together, for example two or more of the rotating members shown in FIG. 19 can be stacked vertically in the tank. When multiple rotating members are used, they can be configured to rotate in the same direction or in opposite directions, and at the same speed or different speeds.

Materials

Biomass Materials

The biomass can be, e.g., a cellulosic or lignocellulosic material. Such materials include paper and paper products (e.g., polycoated paper and Kraft paper), wood, wood-related materials, e.g., particle board, grasses, rice hulls, bagasse, jute, hemp, flax, bamboo, sisal, abaca, straw, switchgrass, alfalfa, hay, corn cobs, corn stover, coconut hair; and materials high in α-cellulose content, e.g., cotton. Feedstocks can be obtained from virgin scrap textile materials, e.g., remnants, post consumer waste, e.g., rags. When paper products are used they can be virgin materials, e.g., scrap virgin materials, or they can be post-consumer waste. Aside from virgin raw materials, post-consumer, industrial (e.g., offal), and processing waste (e.g., effluent from paper processing) can also be used as fiber sources. Biomass feedstocks can also be obtained or derived from human (e.g., sewage), animal or plant wastes. Additional cellulosic and lignocellulosic materials have been described in U.S. Pat. Nos. 6,448,307, 6,258,876, 6,207,729, 5,973,035 and 5,952,105.

In some embodiments, the biomass material includes a carbohydrate that is or includes a material having one or more β-1,4-linkages and having a number average molecular weight between about 3,000 and 50,000. Such a carbohydrate is or includes cellulose (I), which is derived from (β-glucose 1) through condensation of β(1,4)-glycosidic bonds. This linkage contrasts itself with that for α(1,4)-glycosidic bonds present in starch and other carbohydrates.

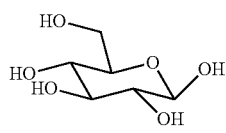

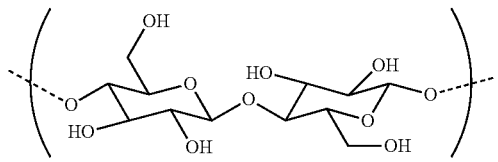

Starchy materials include starch itself, e.g., corn starch, wheat starch, potato starch or rice starch, a derivative of starch, or a material that includes starch, such as an edible food product or a crop. For example, the starchy material can be arracacha, buckwheat, banana, barley, cassava, kudzu, oca, sago, sorghum, regular household potatoes, sweet potato, taro, yams, or one or more beans, such as favas, lentils or peas. Blends of any two or more starchy materials are also starchy materials.

In some cases the biomass is a microbial material. Microbial sources include, but are not limited to, any naturally occurring or genetically modified microorganism or organism that contains or is capable of providing a source of carbohydrates (e.g., cellulose), for example, protists, e.g., animal protists (e.g., protozoa such as flagellates, amoeboids, ciliates, and sporozoa) and plant protists (e.g., algae such alveolates, chlorarachniophytes, cryptomonads, euglenids, glaucophytes, haptophytes, red algae, stramenopiles, and viridaeplantae). Other examples include seaweed, plankton (e.g., macroplankton, mesoplankton, microplankton, nanoplankton, picoplankton, and femptoplankton), phytoplankton, bacteria (e.g., gram positive bacteria, gram negative bacteria, and extremophiles), yeast and/or mixtures of these. In some instances, microbial biomass can be obtained from natural sources, e.g., the ocean, lakes, bodies of water, e.g., salt water or fresh water, or on land. Alternatively or in addition, microbial biomass can be obtained from culture systems, e.g., large scale dry and wet culture systems.

Saccharifying Agents

Suitable enzymes include cellobiases and cellulases capable of degrading biomass.

Suitable cellobiases include a cellobiase from *Aspergillus niger* sold under the tradename NOVOZYME 188™.

Cellulases are capable of degrading biomass, and may be of fungal or bacterial origin. Suitable enzymes include cellulases from the genera *Bacillus, Pseudomonas, Humicola, Fusarium, Thielavia, Acremonium, Chrysosporium* and *Trichoderma*, and include species of *Humicola, Coprinus, Thielavia, Fusarium, Myceliophthora, Acremonium, Cephalosporium, Scytalidium, Penicillium* or *Aspergillus* (see, e.g., EP 458162), especially those produced by a strain selected from the species *Humicola insolens* (reclassified as *Scytalidium thermophilum*, see, e.g., U.S. Pat. No. 4,435,307), *Coprinus cinereus, Fusarium oxysporum, Myceliophthora thermophila, Meripilus giganteus, Thielavia terrestris, Acremonium* sp., *Acremonium persicinum, Acremonium acremonium, Acremonium brachypenium, Acremonium dichromosporum, Acremonium obclavatum, Acremonium pinkertoniae, Acremonium roseogriseum, Acremonium incoloratum,* and *Acremonium furatum*; preferably from the species *Humicola insolens* DSM 1800, *Fusarium oxysporum* DSM 2672, *Myceliophthora thermophila* CBS 117.65, *Cephalosporium* sp. RYM-202, *Acremonium* sp. CBS 478.94, *Acremonium* sp. CBS 265.95, *Acremonium persicinum* CBS 169.65, *Acremonium acremonium* AHU 9519, *Cephalosporium* sp. CBS 535.71, *Acremonium brachypenium* CBS 866.73, *Acremonium dichromosporum* CBS 683.73, *Acremonium obclavatum* CBS 311.74, *Acremonium pinkertoniae* CBS 157.70, *Acremonium roseogriseum* CBS 134.56, *Acremonium incoloratum* CBS 146.62, and *Acremonium furatum* CBS 299.70H. Cellulolytic enzymes may also be obtained from *Chrysosporium*, preferably a strain of *Chrysosporium lucknowense*. Additionally, *Trichoderma* (particularly *Trichoderma viride, Trichoderma reesei*, and *Trichoderma koningii*), alkalophilic *Bacillus* (see, for example, U.S. Pat. No. 3,844,890 and EP 458162), and *Streptomyces* (see, e.g., EP 458162) may be used.

Enzyme complexes may be utilized, such as those available from Genencore under the tradename ACCELLERASE®, for example, Accellerase® 1500 enzyme complex. Accellerase 1500 enzyme complex contains multiple enzyme activities, mainly exoglucanase, endoglucanase (2200-2800 CMC U/g), hemi-cellulase, and beta-glucosidase (525-775 pNPG U/g), and has a pH of 4.6 to 5.0. The endoglucanase activity of the enzyme complex is expressed in carboxymethylcellulose activity units (CMC U), while the beta-glucosidase activity is reported in pNP-glucoside activity units (pNPG U). In one embodiment, a blend of Accellerase® 1500 enzyme complex and NOVOZYME™ 188 cellobiase is used.

In some implementations, the saccharifying agent comprises an acid, e.g., a mineral acid. When an acid is used, co-products may be generated that are toxic to microorganisms, in which case the process can further include removing such co-products. Removal may be performed using an activated carbon, e.g., activated charcoal, or other suitable techniques.

Fermentation Agents

The microorganism(s) used in fermentation can be natural microorganisms and/or engineered microorganisms. For example, the microorganism can be a bacterium, e.g., a cellulolytic bacterium, a fungus, e.g., a yeast, a plant or a protist, e.g., an algae, a protozoa or a fungus-like protist, e.g., a slime mold. When the organisms are compatible, mixtures of organisms can be utilized.

Suitable fermenting microorganisms have the ability to convert carbohydrates, such as glucose, xylose, arabinose, mannose, galactose, oligosaccharides or polysaccharides into fermentation products. Fermenting microorganisms include strains of the genus *Sacchromyces* spp. e.g., *Sacchromyces cerevisiae* (baker's yeast), *Saccharomyces distaticus, Saccharomyces uvarum*; the genus *Kluyveromyces*, e.g., species *Kluyveromyces marxianus, Kluyveromyces fragilis*; the genus *Candida*, e.g., *Candida pseudotropicalis*, and *Candida brassicae, Pichia stipitis* (a relative of *Candida shehatae*, the genus *Clavispora*, e.g., species *Clavispora lusitaniae* and *Clavispora opuntiae*, the genus *Pachysolen*, e.g., species *Pachysolen tannophilus*, the genus *Bretannomyces*, e.g., species *Bretannomyces clausenii* (Philippidis, G. P., 1996, Cellulose bioconversion technology, in Handbook on Bioethanol: Production and Utilization, Wyman, C. E., ed., Taylor & Francis, Washington, D.C., 179-212).

Commercially available yeasts include, for example, Red Star®/Lesaffre Ethanol Red (available from Red Star/Lesaffre, USA), FALI® (available from Fleischmann's Yeast, a division of Burns Philip Food Inc., USA), SUPERSTART® (available from Alltech, now Lalemand), GERT STRAND® (available from Gert Strand AB, Sweden) and FERMOL® (available from DSM Specialties).

Bacteria may also be used in fermentation, e.g., *Zymomonas mobilis* and *Clostridium thermocellum* (Philippidis, 1996, supra).

Additives

Antibiotics

While it is generally preferred to have a high sugar concentration in the saccharified solution, lower concentrations may be used, in which case it may be desirable to add an antimicrobial additive, e.g., a broad spectrum antibiotic, in a low concentration, e.g., 50 to 150 ppm. Other suitable antibiotics include amphotericin B, ampicillin, chloramphenicol, ciprofloxacin, gentamicin, hygromycin B, kanamycin, neomycin, penicillin, puromycin, streptomycin. Antibiotics will inhibit growth of microorganisms during transport and storage, and can be used at appropriate concentrations, e.g., between 15 and 1000 ppm by weight, e.g., between 25 and 500 ppm, or between 50 and 150 ppm. If desired, an antibiotic can be included even if the sugar concentration is relatively high.

Surfactants

The addition of surfactants can enhance the rate of saccharification. Examples of surfactants include non-ionic surfactants, such as a Tween® 20 or Tween® 80 polyethylene glycol surfactants, ionic surfactants, or amphoteric surfactants. Other suitable surfactants include octylphenol ethoxylates such as the TRITON™ X series nonionic surfactants commercially available from Dow Chemical. A surfactant can also be added to keep the sugar that is being produced in solution, particularly in high concentration solutions.

Saccharification Medium

In one embodiment, the medium has the following concentrations of components:

| | |
|---|---|
| Yeast nitrogen base | 1.7 g/L |
| Urea | 2.27 g/L |
| Peptone | 6.56 g/L |
| Tween ® 80 surfactant | 10 g/L |

Physical Treatment of Feedstock

In some implementations, the feedstock is physically treated prior to saccharification and/or fermentation. Physical treatment processes can include one or more of any of those described herein, such as mechanical treatment, chemical treatment, irradiation, sonication, oxidation, pyrolysis or steam explosion. Treatment methods can be used in combinations of two, three, four, or even all of these technologies (in any order). When more than one treatment method is used, the methods can be applied at the same time or at different times. Other processes that change a molecular structure of a biomass feedstock may also be used, alone or in combination with the processes disclosed herein.

Mechanical Treatments

In some cases, methods can include mechanically treating the biomass feedstock. Mechanical treatments include, for example, cutting, milling, pressing, grinding, shearing and chopping. Milling may include, for example, ball milling, hammer milling, rotor/stator dry or wet milling, or other types of milling. Other mechanical treatments include, e.g., stone grinding, cracking, mechanical ripping or tearing, pin grinding or air attrition milling.

Mechanical treatment can be advantageous for "opening up," "stressing," breaking and shattering the cellulosic or lignocellulosic materials, making the cellulose of the materials more susceptible to chain scission and/or reduction of crystallinity. The open materials can also be more susceptible to oxidation when irradiated.

In some cases, the mechanical treatment may include an initial preparation of the feedstock as received, e.g., size reduction of materials, such as by cutting, grinding, shearing, pulverizing or chopping. For example, in some cases, loose feedstock (e.g., recycled paper, starchy materials, or switchgrass) is prepared by shearing or shredding.

Alternatively, or in addition, the feedstock material can first be physically treated by one or more of the other physical treatment methods, e.g., chemical treatment, radiation, sonication, oxidation, pyrolysis or steam explosion, and then mechanically treated. This sequence can be advantageous since materials treated by one or more of the other treatments, e.g., irradiation or pyrolysis, tend to be more brittle and, therefore, it may be easier to further change the molecular structure of the material by mechanical treatment.

In some embodiments, the feedstock material is in the form of a fibrous material, and mechanical treatment includes shearing to expose fibers of the fibrous material. Shearing can be performed, for example, using a rotary knife cutter. Other methods of mechanically treating the feedstock include, for example, milling or grinding. Milling may be performed using, for example, a hammer mill, ball mill, colloid mill, conical or cone mill, disk mill, edge mill, Wiley mill or grist mill. Grinding may be performed using, for example, a stone grinder, pin grinder, coffee grinder, or burr grinder. Grinding may be provided, for example, by a reciprocating pin or other element, as is the case in a pin mill. Other mechanical treatment methods include mechanical ripping or tearing, other methods that apply pressure to the material, and air attrition milling. Suitable mechanical treatments further include any other technique that changes the molecular structure of the feedstock.

If desired, the mechanically treated material can be passed through a screen, e.g., having an average opening size of 1.59 mm or less (1/16 inch, 0.0625 inch). In some embodiments, shearing, or other mechanical treatment, and screening are performed concurrently. For example, a rotary knife cutter can be used to concurrently shear and screen the feedstock. The feedstock is sheared between stationary blades and rotating blades to provide a sheared material that passes through a screen, and is captured in a bin.

The cellulosic or lignocellulosic material can be mechanically treated in a dry state (e.g., having little or no free water on its surface), a hydrated state (e.g., having up to ten percent by weight absorbed water), or in a wet state, e.g., having between about 10 percent and about 75 percent by weight water. The fiber source can even be mechanically treated while partially or fully submerged under a liquid, such as water, ethanol or isopropanol.

The cellulosic or lignocellulosic material can also be mechanically treated under a gas (such as a stream or atmosphere of gas other than air), e.g., oxygen or nitrogen, or steam.

If desired, lignin can be removed from any of the fibrous materials that include lignin. Also, to aid in the breakdown of the materials that include cellulose, the material can be treated prior to or during mechanical treatment or irradiation with heat, a chemical (e.g., mineral acid, base or a strong oxidizer such as sodium hypochlorite) and/or an enzyme. For example, grinding can be performed in the presence of an acid.

Mechanical treatment systems can be configured to produce streams with specific morphology characteristics such as, for example, surface area, porosity, bulk density, and, in the case of fibrous feedstocks, fiber characteristics such as length-to-width ratio.

In some embodiments, a BET surface area of the mechanically treated material is greater than 0.1 $m^2/g$, e.g., greater than 0.25 $m^2/g$, greater than 0.5 $m^2/g$, greater than 1.0 $m^2/g$, greater than 1.5 $m^2/g$, greater than 1.75 $m^2/g$, greater than 5.0 $m^2/g$, greater than 10 $m^2/g$, greater than 25 $m^2/g$, greater than 35 $m^2/g$, greater than 50 $m^2/g$, greater than 60 $m^2/g$, greater than 75 $m^2/g$, greater than 100 $m^2/g$, greater than 150 $m^2/g$, greater than 200 $m^2/g$, or even greater than 250 $m^2/g$.

A porosity of the mechanically treated material can be, e.g., greater than 20 percent, greater than 25 percent, greater than 35 percent, greater than 50 percent, greater than 60 percent, greater than 70 percent, greater than 80 percent, greater than 85 percent, greater than 90 percent, greater than 92 percent, greater than 94 percent, greater than 95 percent, greater than 97.5 percent, greater than 99 percent, or even greater than 99.5 percent.

In some embodiments, after mechanical treatment the material has a bulk density of less than 0.25 $g/cm^3$, e.g., 0.20 $g/cm^3$, 0.15 $g/cm^3$, 0.10 $g/cm^3$, 0.05 $g/cm^3$ or less, e.g., 0.025 $g/cm^3$. Bulk density is determined using ASTM D1895B. Briefly, the method involves filling a measuring cylinder of known volume with a sample and obtaining a weight of the sample. The bulk density is calculated by dividing the weight of the sample in grams by the known volume of the cylinder in cubic centimeters.

If the feedstock is a fibrous material the fibers of the mechanically treated material can have a relatively large average length-to-diameter ratio (e.g., greater than 20-to-1), even if they have been sheared more than once. In addition, the fibers of the fibrous materials described herein may have a relatively narrow length and/or length-to-diameter ratio distribution.

As used herein, average fiber widths (e.g., diameters) are those determined optically by randomly selecting approximately 5,000 fibers. Average fiber lengths are corrected length-weighted lengths. BET (Brunauer, Emmet and Teller) surface areas are multi-point surface areas, and porosities are those determined by mercury porosimetry.

If the feedstock is a fibrous material the average length-to-diameter ratio of fibers of the mechanically treated material can be, e.g., greater than 8/1, e.g., greater than 10/1, greater than 15/1, greater than 20/1, greater than 25/1, or greater than 50/1. An average fiber length of the mechanically treated material can be, e.g., between about 0.5 mm and 2.5 mm, e.g., between about 0.75 mm and 1.0 mm, and an average width (e.g., diameter) of the second fibrous material 14 can be, e.g., between about 5 μm and 50 μm, e.g., between about 10 μm and 30 μm.

In some embodiments, if the feedstock is a fibrous material the standard deviation of the fiber length of the mechanically treated material can be less than 60 percent of an average fiber length of the mechanically treated material, e.g., less than 50 percent of the average length, less than 40 percent of the average length, less than 25 percent of the average length, less than 10 percent of the average length, less than 5 percent of the average length, or even less than 1 percent of the average length.

In some situations, it can be desirable to prepare a low bulk density material, densify the material (e.g., to make it easier and less costly to transport to another site), and then revert the material to a lower bulk density state. Densified materials can be processed by any of the methods described herein, or any material processed by any of the methods described herein can be subsequently densified, e.g., as disclosed in U.S. Ser. No. 12/429,045 and WO 2008/073186, the full disclosures of which are incorporated herein by reference.

Radiation Treatment

One or more radiation processing sequences can be used to process the feedstock, and to provide a structurally modified material which functions as input to further processing steps and/or sequences. Irradiation can, for example, reduce the molecular weight and/or crystallinity of feedstock. Radiation can also sterilize the materials, or any media needed to bioprocess the material.

In some embodiments, energy deposited in a material that releases an electron from its atomic orbital is used to irradiate the materials. The radiation may be provided by (1) heavy charged particles, such as alpha particles or protons, (2) electrons, produced, for example, in beta decay or electron beam accelerators, or (3) electromagnetic radiation, for example, gamma rays, x rays, or ultraviolet rays. In one approach, radiation produced by radioactive substances can be used to irradiate the feedstock. In another approach, electromagnetic radiation (e.g., produced using electron beam emitters) can be used to irradiate the feedstock. In some embodiments, any combination in any order or concurrently of (1) through (3) may be utilized. The doses applied depend on the desired effect and the particular feedstock.

In some instances when chain scission is desirable and/or polymer chain functionalization is desirable, particles heavier than electrons, such as protons, helium nuclei, argon ions, silicon ions, neon ions, carbon ions, phoshorus ions, oxygen ions or nitrogen ions can be utilized. When ring-opening chain scission is desired, positively charged particles can be utilized for their Lewis acid properties for enhanced ring-opening chain scission. For example, when maximum oxidation is desired, oxygen ions can be utilized, and when maximum nitration is desired, nitrogen ions can be utilized. The use of heavy particles and positively charged particles is described in U.S. Ser. No. 12/417,699, the full disclosure of which is incorporated herein by reference.

In one method, a first material that is or includes cellulose having a first number average molecular weight ($M_{N1}$) is irradiated, e.g., by treatment with ionizing radiation (e.g., in the form of gamma radiation, X-ray radiation, 100 nm to 280 nm ultraviolet (UV) light, a beam of electrons or other charged particles) to provide a second material that includes cellulose having a second number average molecular weight ($M_{N2}$) lower than the first number average molecular weight. The second material (or the first and second material) can be combined with a microorganism (with or without enzyme treatment) that can utilize the second and/or first material or its constituent sugars or lignin to produce an intermediate or product, such as those described herein.

Since the second material includes cellulose having a reduced molecular weight relative to the first material, and in some instances, a reduced crystallinity as well, the second material is generally more dispersible, swellable and/or soluble, e.g., in a solution containing a microorganism and/or an enzyme. These properties make the second material easier to process and more susceptible to chemical, enzymatic and/or biological attack relative to the first material, which can greatly improve the production rate and/or production level of a desired product, e.g., ethanol.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the starting crystallinity index (prior to irradiation) is from about 40 to about 87.5 percent, e.g., from about 50 to about 75 percent or from about 60 to about 70 percent, and the crystallinity index after irradiation is from about 10 to about 50 percent, e.g., from about 15 to about 45 percent or from about 20 to about 40 percent. However, in some embodiments, e.g., after extensive irradiation, it is possible to have a crystallinity index of lower than 5 percent. In some embodiments, the material after irradiation is substantially amorphous.

In some embodiments, the starting number average molecular weight (prior to irradiation) is from about 200,000 to about 3,200,000, e.g., from about 250,000 to about 1,000,000 or from about 250,000 to about 700,000, and the number average molecular weight after irradiation is from about 50,000 to about 200,000, e.g., from about 60,000 to about 150,000 or from about 70,000 to about 125,000. However, in some embodiments, e.g., after extensive irradiation, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or biological attack. In some embodiments, to increase the level of the oxidation of the second material relative to the first material, the irradiation is performed under an oxidizing environment, e.g., under a blanket of air or oxygen, producing a second material that is more oxidized than the first material. For example, the second material can have more hydroxyl groups, aldehyde groups, ketone groups, ester groups or carboxylic acid groups, which can increase its hydrophilicity.

Ionizing Radiation

Each form of radiation ionizes the carbon-containing material via particular interactions, as determined by the energy of the radiation. Heavy charged particles primarily ionize matter via Coulomb scattering; furthermore, these interactions produce energetic electrons that may further ionize matter. Alpha particles are identical to the nucleus of a helium atom and are produced by the alpha decay of various radioactive nuclei, such as isotopes of bismuth, polonium, astatine, radon, francium, radium, several actinides, such as actinium, thorium, uranium, neptunium, curium, californium, americium, and plutonium.

When particles are utilized, they can be neutral (uncharged), positively charged or negatively charged. When charged, the charged particles can bear a single positive or negative charge, or multiple charges, e.g., one, two, three or even four or more charges. In instances in which chain scission is desired, positively charged particles may be desirable, in part due to their acidic nature. When particles are utilized, the particles can have the mass of a resting electron, or greater, e.g., 500, 1000, 1500, 2000, 10,000 or even 100,000 times the mass of a resting electron. For example, the particles can have a mass of from about 1 atomic unit to about 150 atomic units, e.g., from about 1 atomic unit to about 50 atomic units, or from about 1 to about 25, e.g., 1, 2, 3, 4, 5, 10, 12 or 15 amu. Accelerators used to accelerate the particles can be electrostatic DC, electrodynamic DC, RF linear, magnetic induction linear or continuous wave. For example, cyclotron type accelerators are available from IBA, Belgium, such as the Rhodotron® system, while DC type accelerators are available from RDI, now IBA Industrial, such as the Dynamitron®. Ions and ion accelerators are discussed in Introductory Nuclear Physics, Kenneth S. Krane, John Wiley & Sons, Inc. (1988), Krsto Prelec, FIZIKA B 6 (1997) 4, 177-206, Chu, William T., "Overview of Light-Ion Beam Therapy"

Columbus-Ohio, ICRU-IAEA Meeting, 18-20 Mar. 2006, Iwata, Y. et al., "Alternating-Phase-Focused IH-DTL for Heavy-Ion Medical Accelerators" Proceedings of EPAC 2006, Edinburgh, Scotland and Leaner, C. M. et al., "Status of the Superconducting ECR Ion Source Venus" Proceedings of EPAC 2000, Vienna, Austria.

Gamma radiation has the advantage of a significant penetration depth into a variety of materials. Sources of gamma rays include radioactive nuclei, such as isotopes of cobalt, calcium, technicium, chromium, gallium, indium, iodine, iron, krypton, samarium, selenium, sodium, thalium, and xenon.

Sources of x rays include electron beam collision with metal targets, such as tungsten or molybdenum or alloys, or compact light sources, such as those produced commercially by Lyncean.

Sources for ultraviolet radiation include deuterium or cadmium lamps.

Sources for infrared radiation include sapphire, zinc, or selenide window ceramic lamps.

Sources for microwaves include klystrons, Slevin type RF sources, or atom beam sources that employ hydrogen, oxygen, or nitrogen gases.

In some embodiments, a beam of electrons is used as the radiation source. A beam of electrons has the advantages of high dose rates (e.g., 1, 5, or even 10 Mrad per second), high throughput, less containment, and less confinement equipment. Electrons can also be more efficient at causing chain scission. In addition, electrons having energies of 4-10 MeV can have a penetration depth of 5 to 30 mm or more, such as 40 mm.

Electron beams can be generated, e.g., by electrostatic generators, cascade generators, transformer generators, low energy accelerators with a scanning system, low energy accelerators with a linear cathode, linear accelerators, and pulsed accelerators. Electrons as an ionizing radiation source can be useful, e.g., for relatively thin sections of material, e.g., less than 0.5 inch, e.g., less than 0.4 inch, 0.3 inch, 0.2 inch, or less than 0.1 inch. In some embodiments, the energy of each electron of the electron beam is from about 0.3 MeV to about 2.0 MeV (million electron volts), e.g., from about 0.5 MeV to about 1.5 MeV, or from about 0.7 MeV to about 1.25 MeV.

Electron beam irradiation devices may be procured commercially from Ion Beam Applications, Louvain-la-Neuve, Belgium or the Titan Corporation, San Diego, Calif. Typical electron energies can be 1 MeV, 2 MeV, 4.5 MeV, 7.5 MeV, or 10 MeV. Typical electron beam irradiation device power can be 1 kW, 5 kW, 10 kW, 20 kW, 50 kW, 100 kW, 250 kW, or 500 kW. The level of depolymerization of the feedstock depends on the electron energy used and the dose applied, while exposure time depends on the power and dose. Typical doses may take values of 1 kGy, 5 kGy, 10 kGy, 20 kGy, 50 kGy, 100 kGy, or 200 kGy.

Ion Particle Beams

Particles heavier than electrons can be utilized to irradiate materials, such as carbohydrates or materials that include carbohydrates, e.g., cellulosic materials, lignocellulosic materials, starchy materials, or mixtures of any of these and others described herein. For example, protons, helium nuclei, argon ions, silicon ions, neon ions carbon ions, phosphorus ions, oxygen ions or nitrogen ions can be utilized. In some embodiments, particles heavier than electrons can induce higher amounts of chain scission (relative to lighter particles). In some instances, positively charged particles can induce higher amounts of chain scission than negatively charged particles due to their acidity.

Heavier particle beams can be generated, e.g., using linear accelerators or cyclotrons. In some embodiments, the energy of each particle of the beam is from about 1.0 MeV/atomic unit to about 6,000 MeV/atomic unit, e.g., from about 3 MeV/atomic unit to about 4,800 MeV/atomic unit, or from about 10 MeV/atomic unit to about 1,000 MeV/atomic unit.

In certain embodiments, ion beams used to irradiate carbon-containing materials, e.g., biomass materials, can include more than one type of ion. For example, ion beams can include mixtures of two or more (e.g., three, four or more) different types of ions. Exemplary mixtures can include carbon ions and protons, carbon ions and oxygen ions, nitrogen ions and protons, and iron ions and protons. More generally, mixtures of any of the ions discussed above (or any other ions) can be used to form irradiating ion beams. In particular, mixtures of relatively light and relatively heavier ions can be used in a single ion beam.

In some embodiments, ion beams for irradiating materials include positively-charged ions. The positively charged ions can include, for example, positively charged hydrogen ions (e.g., protons), noble gas ions (e.g., helium, neon, argon), carbon ions, nitrogen ions, oxygen ions, silicon atoms, phosphorus ions, and metal ions such as sodium ions, calcium ions, and/or iron ions. Without wishing to be bound by any theory, it is believed that such positively-charged ions behave chemically as Lewis acid moieties when exposed to materials, initiating and sustaining cationic ring-opening chain scission reactions in an oxidative environment.

In certain embodiments, ion beams for irradiating materials include negatively-charged ions. Negatively charged ions can include, for example, negatively charged hydrogen ions (e.g., hydride ions), and negatively charged ions of various relatively electronegative nuclei (e.g., oxygen ions, nitrogen ions, carbon ions, silicon ions, and phosphorus ions). Without wishing to be bound by any theory, it is believed that such negatively-charged ions behave chemically as Lewis base moieties when exposed to materials, causing anionic ring-opening chain scission reactions in a reducing environment.

In some embodiments, beams for irradiating materials can include neutral atoms. For example, any one or more of hydrogen atoms, helium atoms, carbon atoms, nitrogen atoms, oxygen atoms, neon atoms, silicon atoms, phosphorus atoms, argon atoms, and iron atoms can be included in beams that are used for irradiation of biomass materials. In general, mixtures of any two or more of the above types of atoms (e.g., three or more, four or more, or even more) can be present in the beams.

In certain embodiments, ion beams used to irradiate materials include singly-charged ions such as one or more of $H^+$, $H^-$, $He^+$, $Ne^+$, $C^+$, $C^-$, $O^+$, $O^-$, $N^+$, $N^-$, $Si^+$, $Si^-$, $P^+$, $P^-$, $Na^+$, $Ca^+$, and $Fe^+$. In some embodiments, ion beams can include multiply-charged ions such as one or more of $C^{2+}$, $C^{3+}$, $C^{4+}$, $N^{3+}$, $N^{5+}$, $N^{3-}$, $O^{2+}$, $O^{2-}$, $O_2^{2-}$, $Si^{2+}$, $Si^{4+}$, $Si^{2-}$, and $Si^{4-}$. In general, the ion beams can also include more complex polynuclear ions that bear multiple positive or negative charges. In certain embodiments, by virtue of the structure of the polynuclear ion, the positive or negative charges can be effectively distributed over substantially the entire structure of the ions. In some embodiments, the positive or negative charges can be somewhat localized over portions of the structure of the ions.

Electromagnetic Radiation

In embodiments in which the irradiating is performed with electromagnetic radiation, the electromagnetic radiation can have, e.g., energy per photon (in electron volts) of greater than $10^2$ eV, e.g., greater than $10^3$, $10^4$, $10^5$, $10^6$, or even greater than $10^7$ eV. In some embodiments, the electromagnetic radiation has energy per photon of between $10^4$ and $10^7$, e.g., between $10^5$ and $10^6$ eV. The electromagnetic radiation can have a frequency of, e.g., greater than $10^{16}$ hz, greater than $10^{17}$ hz, $10^{18}$, $10^{19}$, $10^{20}$, or even greater than $10^{21}$ hz. In some embodiments, the electromagnetic radiation has a frequency of between $10^{18}$ and $10^{22}$ hz, e.g., between $10^{19}$ to $10^{21}$ hz.

Quenching and Controlled Functionalization

After treatment with ionizing radiation, any of the materials or mixtures described herein may become ionized; that is, the treated material may include radicals at levels that are detectable with an electron spin resonance spectrometer. If ionized biomass remains in the atmosphere, it will be oxidized, such as to an extent that carboxylic acid groups are generated by reacting with the atmospheric oxygen. In some instances with some materials, such oxidation is desired because it can aid in the further breakdown in molecular weight of the carbohydrate-containing biomass, and the oxidation groups, e.g., carboxylic acid groups can be helpful for solubility and microorganism utilization in some instances. However, since the radicals can "live" for some time after irradiation, e.g., longer than 1 day, 5 days, 30 days, 3 months, 6 months or even longer than 1 year, material properties can continue to change over time, which in some instances, can be undesirable. Thus, it may be desirable to quench the ionized material.

After ionization, any biomass material that has been ionized can be quenched to reduce the level of radicals in the ionized biomass, e.g., such that the radicals are no longer detectable with the electron spin resonance spectrometer. For example, the radicals can be quenched by the application of a sufficient pressure to the biomass and/or by utilizing a fluid in contact with the ionized biomass, such as a gas or liquid, that reacts with (quenches) the radicals. Using a gas or liquid to at least aid in the quenching of the radicals can be used to functionalize the ionized biomass with a desired amount and kind of functional groups, such as carboxylic acid groups, enol groups, aldehyde groups, nitro groups, nitrile groups, amino groups, alkyl amino groups, alkyl groups, chloroalkyl groups or chlorofluoroalkyl groups.

In some instances, such quenching can improve the stability of some of the ionized biomass materials. For example, quenching can improve the resistance of the biomass to oxidation. Functionalization by quenching can also improve the solubility of any biomass described herein, can improve its thermal stability, and can improve material utilization by various microorganisms. For example, the functional groups imparted to the biomass material by the quenching can act as receptor sites for attachment by microorganisms, e.g., to enhance cellulose hydrolysis by various microorganisms.

In some embodiments, quenching includes an application of pressure to the biomass, such as by mechanically deforming the biomass, e.g., directly mechanically compressing the biomass in one, two, or three dimensions, or applying pressure to a fluid in which the biomass is immersed, e.g., isostatic pressing. In such instances, the deformation of the material itself brings radicals, which are often trapped in crystalline domains, in close enough proximity so that the radicals can recombine, or react with another group. In some instances, the pressure is applied together with the application of heat, such as a sufficient quantity of heat to elevate the temperature of the biomass to above a melting point or softening point of a component of the biomass, such as lignin, cellulose or hemicellulose. Heat can improve molecular mobility in the material, which can aid in the quenching of the radicals. When pressure is utilized to quench, the pressure can be greater than about 1000 psi, such as greater than about 1250 psi, 1450 psi, 3625 psi, 5075 psi, 7250 psi, 10000 psi or even greater than 15000 psi. In some embodiments, quenching includes contacting the biomass with a fluid, such as a liquid or gas, e.g., a gas capable of reacting with the radicals, such as acetylene or a mixture of acetylene in nitrogen, ethylene, chlorinated ethylenes or chlorofluoroethylenes, propylene or mixtures of these gases. In other particular embodiments, quenching includes contacting the biomass with a liquid, e.g., a liquid soluble in, or at least capable of penetrating into the biomass and reacting with the radicals, such as a diene, such as 1,5-cyclooctadiene. In some specific embodiments, quenching includes contacting the biomass with an antioxidant, such as Vitamin E. If desired, the biomass feedstock can include an antioxidant dispersed therein, and the quenching can come from contacting the antioxidant dispersed in the biomass feedstock with the radicals.

Functionalization can be enhanced by utilizing heavy charged ions, such as any of the heavier ions described herein. For example, if it is desired to enhance oxidation, charged oxygen ions can be utilized for the irradiation. If nitrogen functional groups are desired, nitrogen ions or anions that include nitrogen can be utilized. Likewise, if sulfur or phosphorus groups are desired, sulfur or phosphorus ions can be used in the irradiation.

Doses

In some instances, the irradiation is performed at a dosage rate of greater than about 0.25 Mrad per second, e.g., greater than about 0.5, 0.75, 1.0, 1.5, 2.0, or even greater than about 2.5 Mrad per second. In some embodiments, the irradiating is performed at a dose rate of between 5.0 and 1500.0 kilorads/hour, e.g., between 10.0 and 750.0 kilorads/hour or between 50.0 and 350.0 kilorads/hour. In some embodiments, the irradiating (with any radiation source or a combination of sources) is performed until the material receives a dose of at least 0.1 Mrad, at least 0.25 Mrad, e.g., at least 1.0 Mrad, at least 2.5 Mrad, at least 5.0 Mrad, at least 10.0 Mrad, at least 60 Mrad or at least 100 Mrad. In some embodiments, the irradiating is performed until the material receives a dose of from about 0.1 Mrad to about 500 Mrad, from about 0.5 Mrad to about 200 Mrad, from about 1 Mrad to about 100 Mrad, or from about 5 Mrad to about 60 Mrad. In some embodiments, a relatively low dose of radiation is applied, e.g., less than 60 Mrad.

Sonication

Sonication can reduce the molecular weight and/or crystallinity of materials, such as one or more of any of the materials described herein, e.g., one or more carbohydrate sources, such as cellulosic or lignocellulosic materials, or starchy materials. Sonication can also be used to sterilize the materials. As discussed above with regard to radiation, the process parameters used for sonication can be varied depending on various factors, e.g., depending on the lignin content of the feedstock. For example, feedstocks with higher lignin levels generally require a higher residence time and/or energy level, resulting in a higher total energy delivered to the feedstock.

In one method, a first material that includes cellulose having a first number average molecular weight ($M_{N1}$) is dispersed in a medium, such as water, and sonicated and/or otherwise cavitated, to provide a second material that includes cellulose having a second number average molecular weight ($M_{N2}$) lower than the first number average molecular weight. The second material (or the first and second material in certain embodiments) can be combined with a microorganism (with or without enzyme treatment) that can utilize the second and/or first material to produce an intermediate or product.

Since the second material includes cellulose having a reduced molecular weight relative to the first material, and in some instances, a reduced crystallinity as well, the second material is generally more dispersible, swellable, and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the starting crystallinity index (prior to sonication) is from about 40 to about 87.5 percent, e.g., from about 50 to about 75 percent or from about 60 to about 70 percent, and the crystallinity index after sonication is from about 10 to about 50 percent, e.g., from about 15 to about 45 percent or from about 20 to about 40 percent. However, in certain embodiments, e.g., after extensive sonication, it is possible to have a crystallinity index of lower than 5 percent. In some embodiments, the material after sonication is substantially amorphous.

In some embodiments, the starting number average molecular weight (prior to sonication) is from about 200,000 to about 3,200,000, e.g., from about 250,000 to about 1,000,000 or from about 250,000 to about 700,000, and the number average molecular weight after sonication is from about 50,000 to about 200,000, e.g., from about 60,000 to about 150,000 or from about 70,000 to about 125,000. However, in some embodiments, e.g., after extensive sonication, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the material's susceptibility to chemical, enzymatic or microbial attack. In some embodiments, to increase the level of the oxidation of the second material relative to the first material, the sonication is performed in an oxidizing medium, producing a second material that is more oxidized than the first material. For example, the second material can have more hydroxyl groups, aldehyde groups, ketone groups, ester groups or carboxylic acid groups, which can increase its hydrophilicity.

In some embodiments, the sonication medium is an aqueous medium. If desired, the medium can include an oxidant, such as a peroxide (e.g., hydrogen peroxide), a dispersing agent and/or a buffer. Examples of dispersing agents include ionic dispersing agents, e.g., sodium lauryl sulfate, and non-ionic dispersing agents, e.g., poly(ethylene glycol).

In other embodiments, the sonication medium is non-aqueous. For example, the sonication can be performed in a hydrocarbon, e.g., toluene or heptane, an ether, e.g., diethyl ether or tetrahydrofuran, or even in a liquefied gas such as argon, xenon, or nitrogen.

Pyrolysis

One or more pyrolysis processing sequences can be used to process carbon-containing materials from a wide variety of different sources to extract useful substances from the materials, and to provide partially degraded materials which function as input to further processing steps and/or sequences. Pyrolysis can also be used to sterilize the materials. Pyrolysis conditions can be varied depending on the characteristics of the feedstock and/or other factors. For example, feedstocks with higher lignin levels may require a higher temperature, longer residence time, and/or introduction of higher levels of oxygen during pyrolysis.

In one example, a first material that includes cellulose having a first number average molecular weight ($M_{N1}$) is pyrolyzed, e.g., by heating the first material in a tube furnace (in the presence or absence of oxygen), to provide a second material that includes cellulose having a second number average molecular weight ($M_{N2}$) lower than the first number average molecular weight.

Since the second material includes cellulose having a reduced molecular weight relative to the first material, and in some instances, a reduced crystallinity as well, the second material is generally more dispersible, swellable and/or soluble, e.g., in a solution containing a microorganism.

In some embodiments, the second number average molecular weight ($M_{N2}$) is lower than the first number average molecular weight ($M_{N1}$) by more than about 10 percent, e.g., more than about 15, 20, 25, 30, 35, 40, 50 percent, 60 percent, or even more than about 75 percent.

In some instances, the second material includes cellulose that has a crystallinity ($C_2$) that is lower than the crystallinity ($C_1$) of the cellulose of the first material. For example, ($C_2$) can be lower than ($C_1$) by more than about 10 percent, e.g., more than about 15, 20, 25, 30, 35, 40, or even more than about 50 percent.

In some embodiments, the starting crystallinity (prior to pyrolysis) is from about 40 to about 87.5 percent, e.g., from about 50 to about 75 percent or from about 60 to about 70 percent, and the crystallinity index after pyrolysis is from about 10 to about 50 percent, e.g., from about 15 to about 45 percent or from about 20 to about 40 percent. However, in certain embodiments, e.g., after extensive pyrolysis, it is possible to have a crystallinity index of lower than 5 percent. In some embodiments, the material after pyrolysis is substantially amorphous.

In some embodiments, the starting number average molecular weight (prior to pyrolysis) is from about 200,000 to about 3,200,000, e.g., from about 250,000 to about 1,000,000 or from about 250,000 to about 700,000, and the number average molecular weight after pyrolysis is from about 50,000 to about 200,000, e.g., from about 60,000 to about 150,000 or from about 70,000 to about 125,000. However, in some embodiments, e.g., after extensive pyrolysis, it is possible to have a number average molecular weight of less than about 10,000 or even less than about 5,000.

In some embodiments, the second material can have a level of oxidation ($O_2$) that is higher than the level of oxidation ($O_1$) of the first material. A higher level of oxidation of the material can aid in its dispersability, swellability and/or solubility, further enhancing the susceptibility of the material to chemical, enzymatic or microbial attack. In some embodiments, to increase the level of the oxidation of the second material relative to the first material, the pyrolysis is performed in an oxidizing environment, producing a second material that is more oxidized than the first material. For example, the second material can have more hydroxyl groups, aldehyde groups, ketone groups, ester groups or carboxylic acid groups, than the first material, thereby increasing the hydrophilicity of the material.

In some embodiments, the pyrolysis of the materials is continuous. In other embodiments, the material is pyrolyzed for a pre-determined time, and then allowed to cool for a second pre-determined time before pyrolyzing again.

Oxidation

One or more oxidative processing sequences can be used to process carbon-containing materials from a wide variety of different sources to extract useful substances from the materials, and to provide partially degraded and/or altered material which functions as input to further processing steps and/or sequences. The oxidation conditions can be varied, e.g., depending on the lignin content of the feedstock, with a higher degree of oxidation generally being desired for higher lignin content feedstocks.

In one method, a first material that includes cellulose having a first number average molecular weight ($M_{N1}$) and having a first oxygen content ($O_1$) is oxidized, e.g., by heating the first material in a stream of air or oxygen-enriched air, to provide a second material that includes cellulose having a second number average molecular weight ($M_{N2}$) and having a second oxygen content ($O_2$) higher than the first oxygen content ($O_1$).

The second number average molecular weight of the second material is generally lower than the first number average molecular weight of the first material. For example, the molecular weight may be reduced to the same extent as discussed above with respect to the other physical treatments. The crystallinity of the second material may also be reduced to the same extent as discussed above with respect to the other physical treatments.

In some embodiments, the second oxygen content is at least about five percent higher than the first oxygen content, e.g., 7.5 percent higher, 10.0 percent higher, 12.5 percent higher, 15.0 percent higher or 17.5 percent higher. In some preferred embodiments, the second oxygen content is at least about 20.0 percent higher than the first oxygen content of the first material. Oxygen content is measured by elemental analysis by pyrolyzing a sample in a furnace operating at 1300° C. or higher. A suitable elemental analyzer is the LECO CHNS-932 analyzer with a VTF-900 high temperature pyrolysis furnace.

Generally, oxidation of a material occurs in an oxidizing environment. For example, the oxidation can be effected or aided by pyrolysis in an oxidizing environment, such as in air or argon enriched in air. To aid in the oxidation, various chemical agents, such as oxidants, acids or bases can be added to the material prior to or during oxidation. For example, a peroxide (e.g., benzoyl peroxide) can be added prior to oxidation.

Some oxidative methods of reducing recalcitrance in a biomass feedstock employ Fenton-type chemistry. Such methods are disclosed, for example, in U.S. Ser. No. 12/639,289, the complete disclosure of which is incorporated herein by reference.

Exemplary oxidants include peroxides, such as hydrogen peroxide and benzoyl peroxide, persulfates, such as ammonium persulfate, activated forms of oxygen, such as ozone, permanganates, such as potassium permanganate, perchlorates, such as sodium perchlorate, and hypochlorites, such as sodium hypochlorite (household bleach).

In some situations, pH is maintained at or below about 5.5 during contact, such as between 1 and 5, between 2 and 5, between 2.5 and 5 or between about 3 and 5. Oxidation conditions can also include a contact period of between 2 and 12 hours, e.g., between 4 and 10 hours or between 5 and 8 hours. In some instances, temperature is maintained at or below 300° C., e.g., at or below 250, 200, 150, 100 or 50° C. In some instances, the temperature remains substantially ambient, e.g., at or about 20-25° C.

In some embodiments, the one or more oxidants are applied as a gas, such as by generating ozone in-situ by irradiating the material through air with a beam of particles, such as electrons.

In some embodiments, the mixture further includes one or more hydroquinones, such as 2,5-dimethoxyhydroquinone (DMHQ) and/or one or more benzoquinones, such as 2,5-dimethoxy-1,4-benzoquinone (DMBQ), which can aid in electron transfer reactions.

In some embodiments, the one or more oxidants are electrochemically-generated in-situ. For example, hydrogen peroxide and/or ozone can be electro-chemically produced within a contact or reaction vessel.

Other Processes to Solubilize, Reduce Recalcitrance or to Functionalize

Any of the processes of this paragraph can be used alone without any of the processes described herein, or in combination with any of the processes described herein (in any order): steam explosion, chemical treatment (e.g., acid treatment (including concentrated and dilute acid treatment with mineral acids, such as sulfuric acid, hydrochloric acid and organic acids, such as trifluoroacetic acid) and/or base treatment (e.g., treatment with lime or sodium hydroxide)), UV treatment, screw extrusion treatment (see, e.g., U.S. patent application Ser. No. 61/115,398, filed Nov. 17, 2008, solvent treatment (e.g., treatment with ionic liquids) and freeze milling (see, e.g., U.S. Ser. No. 12/502,629).

Production of Fuels, Acids, Esters and/or Other Products

After one or more of the processing steps discussed above have been performed on the biomass, the complex carbohydrates contained in the cellulose and hemicellulose fractions can be processed into fermentable sugars using a saccharification process, as discussed above.

After the resulting sugar solution has been transported to a manufacturing facility, the sugars can be converted into a variety of products, such as alcohols, e.g., ethanol, or organic acids. The product obtained depends upon the microorganism utilized and the conditions under which the bioprocessing occurs. These steps can be performed, for example, utilizing the existing equipment of the corn-based ethanol manufacturing facility.

The mixing processes and equipment discussed herein may also be used during bioprocessing, if desired. Advantageously, the mixing systems described herein do not impart high shear to the liquid, and do not significantly raise the overall temperature of the liquid. As a result, the microorganisms used in bioprocessing are maintained in a viable condition throughout the process. Mixing may enhance the reaction rate and improve the efficiency of the process.

Generally, fermentation utilizes various microorganisms. The sugar solution produced by saccharification of lignocellulosic materials will generally contain xylose as well as glucose. It may be desirable to remove the xylose, e.g., by chromatography, as some commonly used microorganisms (e.g., yeasts) do not act on xylose. The xylose may be collected and utilized in the manufacture of other products, e.g., animal feeds and the sweetener Xylitol. The xylose may be removed prior to or after delivery of the sugar solution to the manufacturing facility where fermentation will be performed.

The microorganism can be a natural microorganism or an engineered microorganism, e.g., any of the microorganisms discussed in the Materials section herein.

The optimum pH for yeast is from about pH 4 to 5, while the optimum pH for *Zymomonas* is from about pH 5 to 6. Typical fermentation times are about 24 to 96 hours with temperatures in the range of 26° C. to 40° C., however thermophilic microorganisms prefer higher temperatures.

Carboxylic acid groups generally lower the pH of the fermentation solution, tending to inhibit fermentation with some microorganisms, such *Pichia stipitis*. Accordingly, it is in some cases desirable to add base and/or a buffer, before or during fermentation, to bring up the pH of the solution. For example, sodium hydroxide or lime can be added to the fermentation medium to elevate the pH of the medium to range that is optimum for the microorganism utilized.

Fermentation is generally conducted in an aqueous growth medium, which can contain a nitrogen source or other nutrient source, e.g., urea, along with vitamins and trace minerals and metals. It is generally preferable that the growth medium be sterile, or at least have a low microbial load, e.g., bacterial count. Sterilization of the growth medium may be accomplished in any desired manner. However, in preferred implementations, sterilization is accomplished by irradiating the growth medium or the individual components of the growth medium prior to mixing. The dosage of radiation is generally as low as possible while still obtaining adequate results, in order to minimize energy consumption and resulting cost. For example, in many instances, the growth medium itself or components of the growth medium can be treated with a radiation dose of less than 5 Mrad, such as less than 4, 3, 2 or 1 Mrad. In specific instances, the growth medium is treated with a dose of between about 1 and 3 Mrad.

In some embodiments, all or a portion of the fermentation process can be interrupted before the low molecular weight sugar is completely converted to ethanol. The intermediate fermentation products include high concentrations of sugar and carbohydrates. These intermediate fermentation products can be used in preparation of food for human or animal consumption. Additionally or alternatively, the intermediate fermentation products can be ground to a fine particle size in a stainless-steel laboratory mill to produce a flour-like substance.

Mobile fermentors can be utilized, as described in U.S. Provisional Patent Application Ser. 60/832,735, now Published International Application No. WO 2008/011598. Similarly, the saccharification equipment can be mobile. Further, saccharification and/or fermentation may be performed in part or entirely during transit.

Post-Processing

After fermentation, the resulting fluids can be distilled using, for example, a "beer column" to separate ethanol and other alcohols from the majority of water and residual solids. The vapor exiting the beer column can be, e.g., 35% by weight ethanol and can be fed to a rectification column. A mixture of nearly azeotropic (92.5%) ethanol and water from the rectification column can be purified to pure (99.5%) ethanol using vapor-phase molecular sieves. The beer column bottoms can be sent to the first effect of a three-effect evaporator. The rectification column reflux condenser can provide heat for this first effect. After the first effect, solids can be separated using a centrifuge and dried in a rotary dryer. A portion (25%) of the centrifuge effluent can be recycled to fermentation and the rest sent to the second and third evaporator effects. Most of the evaporator condensate can be returned to the process as fairly clean condensate with a small portion split off to waste water treatment to prevent build-up of low-boiling compounds.

Intermediates and Products

Using the processes described herein, the treated biomass can be converted to one or more products, such as energy, fuels, foods and materials. Specific examples of products include, but are not limited to, hydrogen, alcohols (e.g., monohydric alcohols or dihydric alcohols, such as ethanol, n-propanol or n-butanol), hydrated or hydrous alcohols, e.g., containing greater than 10%, 20%, 30% or even greater than 40% water, xylitol, sugars, biodiesel, organic acids (e.g., acetic acid and/or lactic acid), hydrocarbons, co-products (e.g., proteins, such as cellulolytic proteins (enzymes) or single cell proteins), and mixtures of any of these in any combination or relative concentration, and optionally in combination with any additives, e.g., fuel additives. Other examples include carboxylic acids, such as acetic acid or butyric acid, salts of a carboxylic acid, a mixture of carboxylic acids and salts of carboxylic acids and esters of carboxylic acids (e.g., methyl, ethyl and n-propyl esters), ketones (e.g., acetone), aldehydes (e.g., acetaldehyde), alpha, beta unsaturated acids, such as acrylic acid and olefins, such as ethylene. Other alcohols and alcohol derivatives include propanol, propylene glycol, 1,4-butanediol, 1,3-propanediol, methyl or ethyl esters of any of these alcohols. Other products include methyl acrylate, methylmethacrylate, lactic acid, propionic acid, butyric acid, succinic acid, 3-hydroxypropionic acid, a salt of any of the acids and a mixture of any of the acids and respective salts.

Other intermediates and products, including food and pharmaceutical products, are described in U.S. Ser. No. 12/417,900, the full disclosure of which is hereby incorporated by reference herein.

EXAMPLE a sheared paper feedstock was prepared as follows:

A 1500 pound skid of virgin, half-gallon juice cartons made of un-printed polycoated white Kraft board having a bulk density of 20 lb/ft3 was obtained from International Paper. Each carton was folded flat, and then fed into a 3 hp Flinch Baugh shredder at a rate of approximately 15 to 20 pounds per hour. The shredder was equipped with two 12 inch rotary blades, two fixed blades and a 0.30 inch discharge screen. The gap between the rotary and fixed blades was adjusted to 0.10 inch. The output from the shredder resembled confetti having a width of between 0.1 inch and 0.5 inch, a length of between 0.25 inch and 1 inch and a thickness equivalent to that of the starting material (about 0.075 inch).

The confetti-like material was fed to a Munson rotary knife cutter, Model SC30. Model SC30 is equipped with four rotary blades, four fixed blades, and a discharge screen having ⅛ inch openings. The gap between the rotary and fixed blades was set to approximately 0.020 inch. The rotary knife cutter sheared the confetti-like pieces across the knife-edges, tearing the pieces apart and releasing a fibrous material at a rate of about one pound per hour. The fibrous material had a BET surface area of 0.9748 $m^2/g$+/−0.0167 $m^2/g$, a porosity of 89.0437 percent and a bulk density (@0.53 psia) of 0.1260 g/mL. An average length of the fibers was 1.141 mm and an average width of the fibers was 0.027 mm, giving an average L/D of 42:1.

To saccharify the paper feedstock, first 7 liters of water was added to a vessel. The temperature of the water was maintained at 50° C. throughout the saccharification process, and pH was maintained at 5. The feedstock was added to the water in increments, as shown in the table below. After each addition, mixing was performed until the feedstock was dispersed, after which a mixture of two enzymes was added, again as shown in the table below. (Enzyme 1 was Accellerase® 1500 enzyme complex. Enzyme 2 was Novozyme™ 188 cellobiase enzyme.) After each addition, mixing was initially performed at 10,000 RPM, with the mixer being turned down to 4,000 RPM as soon as the feedstock had been dispersed. An IKA Werks T-50 jet agitator mixer was used, with a 50K-G-45 jet mixing tool.

The feedstock was added in increments because it was necessary to at least partially saccharify the feedstock before more could be added; otherwise the mixture became too difficult to mix. It was observed that less enzyme was needed to obtain a given glucose level than had been required in previous shake-flask experiments. No contamination by undesirable microorganisms such as mold was observed for the first 300 hours. At approximately 300 hours a mold-like organism was observed on the tank walls where sugar concentration was lowest, but not in the tank itself

| Time (hr) | Glucose (Measured (g/L)) | Glucose (Calculated (g/L)) | Enzyme 1 (ml) | Enzyme 2 (ml) | Paper feedstock (g) |
|---|---|---|---|---|---|
| 0 | 0.548 | 54.8 | 100 | 10 | 400 |
| 7 | 0.641 | 64.1 | 100 | 10 | 400 |
| 25 | 0.779 | 77.9 | 100 | 10 | 300 |
| 29 | 0.8 | 80 | 0 | 0 | 0 |
| 50 | 1.11 | 111 | 100 | 10 | 300 |
| 55 | 1.25 | 125 | 0 | 0 | 0 |
| 75 | 1.39 | 139 | 200 | 20 | 1600* |
| 80 | 1.71 | 171 | 0 | 0 | 0 |
| 82 | 1.88 | 188 | 0 | 0 | 0 |
| 106 | 2.03 | 203 | 0 | 0 | 0 |
| 130 | 2.32 | 232 | 0 | 0 | 0 |
| 150 | 2.75 | 275 | 0 | 0 | 0 |

*The 1600 gram addition was made over the course of several hours.

Other Embodiments

A number of embodiments have been described. Nevertheless, it will be understood that various modifications may be made without departing from the spirit and scope of the disclosure.

For example, the jet mixers described herein can be used in any desired combination, and/or in combination with other types of mixers.

The jet mixer(s) may be mounted in any desired position within the tank. With regard to shaft-mounted jet mixers, the shaft may be collinear with the center axis of the tank or may be offset therefrom. For example, if desired the tank may be provided with a centrally mounted mixer of a different type, e.g., a marine impeller or Rushton impeller, and a jet mixer may be mounted in another area of the tank either offset from the center axis or on the center axis. In the latter case one mixer can extend from the top of the tank while the other extends upward from the floor of the tank.

In any of the jet mixing systems described herein, the flow of fluid (liquid and/or gas) through the jet mixer can be continuous or pulsed, or a combination of periods of continuous flow with intervals of pulsed flow. When the flow is pulsed, pulsing can be regular or irregular. In the latter case, the motor that drives the fluid flow can be programmed, for example to provide pulsed flow at intervals to prevent mixing from becoming "stuck." The frequency of pulsed flow can be, for example, from about 0.5 Hz to about 10 Hz, e.g., about 0.5 Hz, 0.75 Hz, 1.0 Hz, 2.0 Hz, 5 Hz, or 10 Hz. Pulsed flow can be provided by turning the motor on and off, and/or by providing a flow diverter that interrupts flow of the fluid.

While tanks have been referred to herein, jet mixing may be used in any type of vessel or container, including lagoons, pools, ponds and the like. If the container in which mixing takes place is an in-ground structure such as a lagoon, it may be lined. The container may be covered, e.g., if it is outdoors, or uncovered.

While biomass feedstocks have been described herein, other feedstocks and mixtures of biomass feedstocks with other feedstocks may be used. For example, some implementations may utilize mixtures of biomass feedstocks with hydrocarbon-containing feedstocks such as those disclosed in U.S. Provisional Application No. 61/226,877, filed Jul. 20, 2009, the full disclosure of which is incorporated by reference herein.

Accordingly, other embodiments are within the scope of the following claims.

What is claimed is:

1. A method comprising:
   converting a particulate feedstock to a product by mixing the particulate feedstock with a microorganism in a fluid medium, using a jet mixer, wherein the jet mixer comprises a jet-flow agitator and the vessel has an arcuate bottom surface and a longitudinal axis of a shaft of the jet-flow agitator is offset laterally from a longitudinal axis of the vessel,
   wherein the particulate feedstock was obtained by saccharification of a lignocellulosic feedstock and comprises a low molecular weight sugar residual solids.

2. The method of claim 1 wherein the fluid medium comprises water.

3. The method of claim 1 wherein the microorganism comprises yeast.

4. The method of claim 1 wherein the jet mixer further comprises a jet aeration type mixer having a delivery nozzle, and wherein converting saccharifiying the feedstock comprises delivering a jet through the delivery nozzle.

5. The method of claim 1 wherein the jet mixer further comprises a suction chamber jet mixer.

6. The method of claim 1 wherein the jet mixer has a power consumption during the execution of the method that is less, under the same conditions, than the power consumption would be if the shaft were aligned with the longitudinal axis.

7. The method of claim 1 wherein the jet mixer comprises an impeller mounted at a distal end of a shaft, and a shroud surrounding the impeller.

8. The method of claim 1 wherein the jet mixer comprises a plurality of jet-flow agitators, each jet-flow agitator being configured to operate reversibly, pumping fluid towards the top of the vessel in a first mode, and towards the bottom of the vessel in a second mode.

9. The method of claim 1 wherein converting comprises fermentation.

10. The method of claim 1 wherein saccharifying comprises agitating a mixture of the lignocellulosic material and a liquid medium with the jet mixer.

* * * * *